(12) United States Patent
Mochida et al.

(10) Patent No.: US 10,370,730 B2
(45) Date of Patent: Aug. 6, 2019

(54) DETECTION METHOD FOR MUTATION IN 93RD AMINO ACID OF HEPATITIS C VIRUS NS5A PROTEIN, AND DETECTION KIT FOR MUTATION IN 93RD AMINO ACID OF HEPATITIS C VIRUS NS54 PROTEIN

(71) Applicant: SAITAMA MEDICAL UNIVERSITY, Iruma-gun, Saitama (JP)

(72) Inventors: Satoshi Mochida, Saitama (JP); Yoshihito Uchida, Saitama (JP); Jun-ichi Kouyama, Saitama (JP); Kayoko Naiki, Saitama (JP)

(73) Assignee: SAITAMA MEDICAL UNIVERSITY, Iruma-Gun, Saitama (JP)

( * ) Notice: Subject to any disclaimer, the term of this patent is extended or adjusted under 35 U.S.C. 154(b) by 349 days.

(21) Appl. No.: 15/103,184

(22) PCT Filed: Dec. 11, 2014

(86) PCT No.: PCT/JP2014/082773
§ 371 (c)(1),
(2) Date: Jun. 9, 2016

(87) PCT Pub. No.: WO2015/087945
PCT Pub. Date: Jun. 18, 2015

(65) Prior Publication Data
US 2018/0163278 A1    Jun. 14, 2018

(30) Foreign Application Priority Data
Dec. 11, 2013  (JP) ................................. 2013 255748
Sep. 12, 2014  (JP) ................................. 2014 185917

(51) Int. Cl.
C12Q 1/70        (2006.01)

(52) U.S. Cl.
CPC ....... C12Q 1/707 (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2003/0050470 A1* | 3/2003 | An | C07H 21/00 536/24.3 |
| 2006/0234223 A1* | 10/2006 | Darvasi | C12Q 1/6883 435/6.12 |
| 2007/0207455 A1* | 9/2007 | Law | C12Q 1/707 435/5 |
| 2007/0298415 A1 | 12/2007 | Uemori et al. | |
| 2009/0098107 A1 | 4/2009 | Tanaka et al. | |

FOREIGN PATENT DOCUMENTS

| | | |
|---|---|---|
| JP | 05-068562 A | 3/1993 |
| JP | 2005-517427 A | 6/2005 |
| JP | 2007-312660 A | 12/2007 |
| WO | WO 03/070750 A2 | 8/2003 |
| WO | WO 2005/056790 A1 | 6/2005 |
| WO | WO 2006/107031 A1 | 10/2006 |

OTHER PUBLICATIONS

Bekkaoui F, Poisson I, Crosby W, Cloney L, Duck P. Cycling probe technology with RNase H attached to an oligonucleotide. Biotechniques. Feb. 1996; 20(2):240-8. (Year: 1996).*
COBAS Taqnnan HCV Assay package insert (2008, Roche). (Year: 2008).*
Hou Y, Luo Q, Chen C, Zhou M. Application of cycleave PCR to the detection of a point mutation (F167Y) in the β2-tubulin gene of Fusarium graminearum. Pest Manag Sci. Sep. 2011; 67(9):1124-8. Epub Apr. 14, 2011. (Year: 2011).*
Karino et al. Characterization of virologic escape in hepatitis C virus genotype 1b patients treated with the direct-acting antivirals daclatasvir and asunaprevir. J Hepatol. Apr. 2013; 58(4):646-54. Epub Nov. 22, 2012. (Year: 2012).*
Genbank Accession No. AF033376—Hepatitis C virus isolate R11 from non-responder patient to interferon alpha therapy, polyprotein mRNA, partial cds, complete NS5A peptide (submitted Nov 7, 1997, retrieved on Apr. 17, 2018 from http://www.ncbi.nlm.nih.gov/nuccore/AF033376). (Year: 1997).*
Genbank Accession No. KF667877—Hepatitis C virus isolate 14529 NS5A gene, partial cds (submitted Sep. 6, 2013, retrieved on Apr. 15, 2018 from http://www.ncbi.nlm.nih.gov/nuccore/KF667877). (Year: 2013).*
Genbank Accession No. JX022773—Hepatitis C virus subtype 1b isolate NR55 NS5A gene, partial cds, (submitted May 4, 2012, retrieved on Apr. 17, 2018 from http://www.ncbi.nlm.nih.gov/nuccore/JX022773). (Year: 2012).*
Genbank Accession No. FR673952—Hepatitis C virus subtype 1a partial gene for polyprotein, E1-E2 region, genomic RNA, isolate patient 73472, clone e73472g (submitted Jul. 28, 2010, retrieved on Apr. 17, 2018 from http://www.ncbi.nlm.nih.gov/nuccore/FR6723952). (Year: 2010).*
Genbank Accession No. AY051292—Hepatitis C virus (isolate India) polyprotein mRNA, complete cds, (submitted Aug. 16, 2001, retrieved on Apr. 17, 2018 from http://www.ncbi.nlm.nih.gov/nuccore/AY051292). (Year: 2001).*

(Continued)

*Primary Examiner* — Christopher M Babic
*Assistant Examiner* — Olayinka A Oyeyemi
(74) *Attorney, Agent, or Firm* — Buchanan, Ingersoll & Rooney PC

(57) ABSTRACT

A method for detecting a mutation in an amino acid at position 93 of a hepatitis C virus NS5A protein, the method including:
  synthesizing cDNA using, as a template, hepatitis C virus RNA in a sample; and
  performing a real-time PCR with a cycling probe method using, as a template, the cDNA;
  wherein a primer set used in the real-time PCR is a certain primer set; and
  wherein probes used in the real-time PCR include certain probes.

20 Claims, 1 Drawing Sheet

Specification includes a Sequence Listing.

(56) References Cited

OTHER PUBLICATIONS

Genbank Accession No. EF139742—Hepatitis C virus isolate JV86 polyprotein gene, partial cds (submitted Nov 24, 2006, retrieved on Apr. 17, 2018 from http://www.ncbi.nlm.nih.gov/nuccore/EF139742). (Year: 2006).*
Genbank Accession No. AF033369—Hepatitis C virus isolate R4 from non-responder patient to interferon alpha therapy, polyprotein mRNA, partial cds, complete NS5A peptide (submitted Nov. 7, 1997, retrieved on Apr. 17, 2018 from http://www.ncbi.nlm.nih.gov/muccore/AF033369). (Year: 1997).*
Genbank Accession No. AF033371—Hepatitis C virus isolate R6 from non-responder patient to interferon alpha therapy, polyprotein mRNA, partial cds, complete NS5A peptide (submitted Nov. 7, 1997, retrieved on Apr. 17, 2018 from http://www.ncbi.nlm.nih.gov/nuccore/AF033371). (Year: 1997).*
Genbank Accession No. AF033370—Hepatitis C virus isolate R5 from non-responder patient to interferon alpha therapy, polyprotein mRNA, partial cds, complete NS5A peptide (submitted Nov. 7, 1997, retrieved on Apr. 17, 2018 from http://www.ncbi.nlm.nih.gov/nuccore/AF033370). (Year: 1997).*
Genbank Accession No. JQ803431—Hepatitis C virus clone 9055.07.D.D6 polyprotein gene, partial cds, (submitted Mar. 20, 2012, retrieved on Apr. 17, 2018 from http://www.ncbi.nlm.nih.gov/nuccore/JQ803431). (Year: 2012).*
SantaLucia Jr, John. Physical principles and visual-OMP software for optimal PCR design. PCR Primer Design. Humana Press, 2007: pp. 3-33. (Year: 2007).*
International Search Report (PCT/ISA/210) dated Mar. 17, 2015, by the Japanese Patent Office as the International Searching Authority for International Application No. PCT/JP2014/082773.
Written Opinion (PCT/ISA/237) dated Mar. 17, 2015, by the Japanese Patent Office as the International Searching Authority for International Application No. PCT/JP2014/082773.
Uchida, Y. et al., "A Novel Simple Assay System to Quantify the Percent HCV-RNA Levels of NS5A Y93H Mutant Strains and Y93 Wild-Type Strains Relative to the Total HCV-RNA Levels to Determine the Indication for Antiviral Therapy with NS5A Inhibitors," PLOS One, vol. 9, Issue 11, pp. 1-8, Nov. 14, 2014.
Hernandez, D. et al., "Natural Prevalence of NS5A Polymorphisms in Subjects Infected with Hepatitis C Virus Genotype 3 and Their Effects on the Antiviral Activity of NS5A Inhibitors", Journal of Clinical Virology, vol. 57, pp. 13-18, May 2013.
Fridell, R.A. et al., "Resistance Analysis of the Hepatitis C Virus NS5A Inhibitor BMS-790052 in an In Vitro Replicon System", Antimicrobial Agents and Chemotherapy, vol. 54, pp. 3641-3650, Sep. 2010.

* cited by examiner

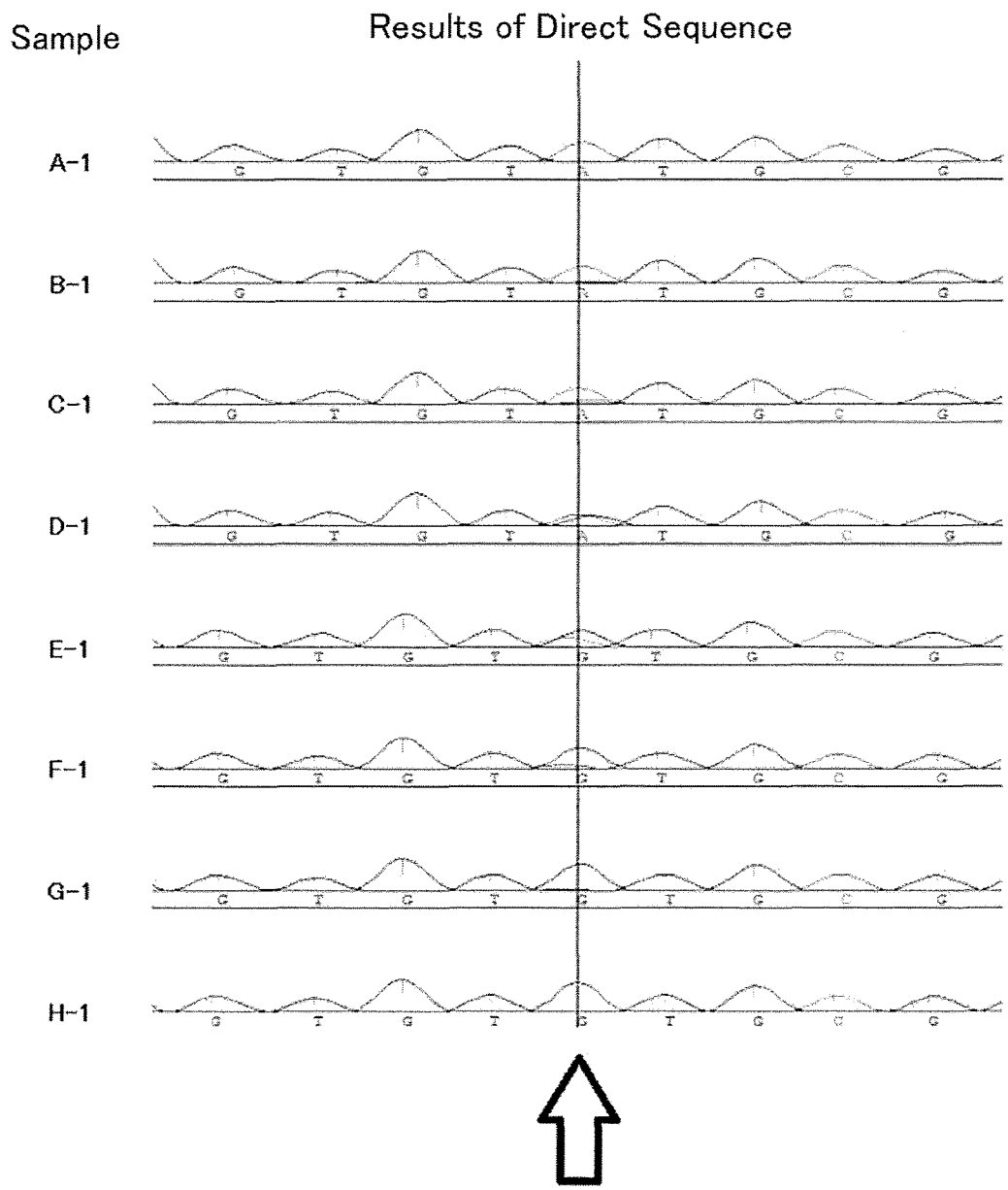

DETECTION METHOD FOR MUTATION IN 93RD AMINO ACID OF HEPATITIS C VIRUS NS5A PROTEIN, AND DETECTION KIT FOR MUTATION IN 93RD AMINO ACID OF HEPATITIS C VIRUS NS54 PROTEIN

TECHNICAL FIELD

The present invention relates to a method for detecting a mutation in an amino acid at position 93 of a hepatitis C virus NS5A protein and a kit for detecting a mutation in an amino acid at position 93 of a hepatitis C virus NS5A protein.

BACKGROUND ART

A hepatitis C virus (hereinafter may be referred to as "HCV") is the main virus causing post-transfusion non-A, non-B hepatitis, and has a positive-strand RNA genome of about 9,500 bases. According to statistics from Ministry of Health, Labour and Welfare, it is estimated that there are 1.5 million or more HCV carriers in Japan in 2000. Patients infected with the HCV have a strong tendency to proceed to chronic hepatitis, hepatic cirrhosis, or hepatic cancer via transient acute hepatitis. It is believed that about 80% of primary hepatic cancer in Japan is HCV-related hepatic cancer. Genotypes of the HCV are classified according to homology of base sequences. There are about 30 genotypes all over the world. In Japan, five genotypes, i.e., type 1a, type 1b, type 2a, type 2b, and type 3a, have been found to infect Japanese or have been detected in Japan. In Japan, types 1b, 2a, and 2b account for most of the five genotypes, while there are few viruses in types 1a or 3a.

Interferons (hereinafter may be referred to as "IFN") have been used for treating chronic hepatitis due to the HCV. Direct-acting antiviral agents have also been used.

An example of the direct-acting antiviral agents includes daclatasvir. The daclatasvir is an inhibitor of an HCV NS5A (non-structural 5A) protein. It has been found that a mutation in an amino acid at position 93 (wild type: tyrosine) of the HCV NS5A protein causes resistance to the daclatasvir (see, e.g., NPL 1). Therefore, there is a need to verify whether the amino acid at position 93 of the HCV NS5A protein is mutated prior to administration of the daclatasvir to patients at a low cost, easily, conveniently, and rapidly.

It has been known that a plurality of HCV variants are mixedly present in a human body. Therefore, when verifying whether the amino acid at position 93 of the HCV NS5A protein in a sample is mutated, there is also a need to quantify HCVs with and without the mutation and determine a mutation rate thereof in addition to the presence or absence of the mutation.

Examples of a method for verifying the presence or absence of the mutation include a direct sequencing method and sequencing with a next-generation sequencer.

Although the direct sequencing method can be inexpensively performed, it is not quantitative. Therefore, there is a problem that it is impossible to quantify a wild-type and a mutated form or to determine the mutation rate thereof by the direct sequencing method. Meanwhile, although the sequencing with a next-generation sequencer is quantitative, a cost per run is very huge. Therefore, there is a problem that it is virtually impossible to use for HCV which is rarely examined in clinical practice and of which genome has a relatively small size.

The HCV is prone to mutation. It has been known that a single genotype includes many variants with a difference of 1 to several hundred bases. Therefore, there is a need for a method for verifying whether the amino acid at position 93 of the HCV NS5A protein in a sample is mutated while suppressing an influence of mutations or variations in the HCV, the method can be applied to various HCVs in the sample.

Therefore, at present, keen demand has arisen for quickly developing a method for quantitatively measuring the presence or absence of a mutation in an amino acid at position 93 of various HCV NS5A proteins in a sample at a low cost, easily, conveniently, and rapidly while suppressing an influence of mutations or variations in HCV.

CITATION LIST

Non-Patent Literature

NPL 1: Robert A. Fridell, et al., Antimicrb Agents Chemother 2010, 54, 3641-50

SUMMARY OF INVENTION

Technical Problem

The present invention aims to solve the above existing problems and achieve the following object. That is, the present invention has an object to provide a method for detecting a mutation in an amino acid at position 93 of a hepatitis C virus NS5A protein and a kit for detecting a mutation in an amino acid at position 93 of a hepatitis C virus NS5A protein, the method and the kit enabling the presence or absence of the mutation in the amino acid at position 93 of various HCV NS5A proteins in a sample to be quantitatively measured at a low cost, easily, conveniently, and rapidly while suppressing an influence of mutations or variations in HCV.

Solution to Problem

Means for solving the above problems are as follows.
<1> A method for detecting a mutation in an amino acid at position 93 of a hepatitis C virus NS5A protein, the method including:
synthesizing cDNA using, as a template, hepatitis C virus RNA in a sample; and
performing a real-time PCR with a cycling probe method using, as a template, the cDNA;
wherein a primer set used in the real-time PCR is a primer set which is designed to be able to amplify a region including a base sequence coding for the amino acid at position 93 of the hepatitis C virus NS5A protein, and
wherein probes used in the real-time PCR includes:
a probe consisting of a base sequence set forth in the following SEQ ID NO: 1 or a probe consisting of a complementary base sequence thereof; and
at least one of a probe consisting of a base sequence set forth in the following SEQ ID NO: 2 or a probe consisting of a complementary base sequence thereof, and a probe consisting of a base sequence set forth in the following SEQ ID NO: 18 or a probe consisting of a complementary base sequence thereof:

aacgcat[a]ca (SEQ ID NO: 1)

aacgcac[a]ca (SEQ ID NO: 2)

acgcac[a]ca (SEQ ID NO: 18)

where in each of the SEQ ID NOs: 1, 2, and 18, a base described in brackets denotes RNA.

<2> A kit for detecting a mutation in an amino acid at position 93 of a hepatitis C virus NS5A protein, the kit including:

a probe consisting of a base sequence set forth in the following SEQ ID NO: 1 or a probe consisting of a complementary base sequence thereof; and at least one of a probe consisting of a base sequence set forth in the following SEQ ID NO: 2 or a probe consisting of a complementary base sequence thereof, and a probe consisting of a base sequence set forth in the following SEQ ID NO: 18 or a probe consisting of a complementary base sequence thereof:

```
                                        (SEQ ID NO: 1)
       aacgcat[a]ca (SEQ ID NO: 2)
       aacgcac[a]ca (SEQ ID NO: 18)
       acgcac[a]ca
``` where in each of the SEQ ID NOs: 1, 2, and 18, a base described in brackets denotes RNA.

Advantageous Effects of Invention

The present invention can solve the above existing problems and achieve the above object. The present invention can provide a method for detecting a mutation in an amino acid at position 93 of a hepatitis C virus NS5A protein and a kit for detecting a mutation in an amino acid at position 93 of a hepatitis C virus NS5A protein, the method and the kit enabling the presence or absence of the mutation in the amino acid at position 93 of various HCV NS5A proteins in a sample to be quantitatively measured at a low cost, easily, conveniently and rapidly while suppressing an influence of mutations or variations in HCV.

BRIEF DESCRIPTION OF DRAWINGS

FIG. 1 is a diagram illustrating results of direct sequencing in Test Example 1.

DESCRIPTION OF EMBODIMENTS (Method, for Detecting Mutation in Amino Acid at Position 93 of Hepatitis C Virus NS5A Protein)

A method for detecting a mutation in an amino acid at position 93 of a hepatitis C virus NS5A protein (hereinafter may be referred to as "HCV NS5A Y93 mutation") according to the present invention includes a cDNA synthesizing step and a real-time PCR step; and, if necessary, further includes other steps.

A genotype of the hepatitis C virus is not particularly limited and may be appropriately selected depending on the intended purpose, but is preferably type 1a, type 1b, type 2a, and type 2b.

<cDNA Synthesizing Step>

The cDNA synthesizing step is a step of synthesizing cDNA using, as a template, hepatitis C virus RNA in a sample.

—Sample—

The sample is not particularly limited and may be appropriately selected depending on the intended purpose. Examples thereof include blood and a tissue of a patient undergoing a test for HCV infection (hereinafter may be referred to as "subject").

A method for collecting the blood or the tissue from the subject is not particularly limited and may be appropriately selected from known methods in the art.

—Preparation of Hepatitis C Virus RNA—

A method for preparing the hepatitis C virus RNA is not particularly limited and may be appropriately selected from known methods in the art. For example, QIAAMP MINELUTE VIRUS SPIN KIT (product of QIAGEN N.V.) may be used.

—Synthesis of cDNA—

A method for synthesizing the cDNA is not particularly limited and may be appropriately selected from known methods in the art. For example, PRIME SCRIPT RT REAGENT KIT (Perfect Real Time) (product of Takara Bio Inc.) or cDNA SYNTHESIS KIT (M-MLV Version) (product of Takara Bio Inc.) may be used.

<Real-Time PCR Step>

The real-time PCR step is a step of performing a real-time PCR with a cycling probe method using, as a template, the cDNA.

<<Cycling Probe Method>>

The real-time PCR with the cycling probe method is a method for determining a base sequence and an amount thereof in a sample using a chimeric probe including RNA and DNA in combination with RNase H.

The probe is modified with a fluorescent substance at one end and with a quenching substance at the other end. After the probe forms a hybrid with a complementary sequence thereof in an amplified product, an RNA moiety is cleaved by RNase H, resulting in intense fluorescence. An amount of the amplified product can be quantified by measuring intensity of the fluorescence.

The fluorescent substance is not particularly limited and may be appropriately selected from known fluorescent substances in the art. Examples thereof include FAM, HEX, and ROX.

The quenching substance is not particularly limited and may be appropriately selected from known quenching substances in the art. Examples thereof include ECLIPSE DARK QUENCHER (product of Epoch Biosciences), BHQ1 DARK QUENCHER (product of BIOSERCH TECHNOLOGIES), and BHQ2 DARK QUENCHER (product of BIOSERCH TECHNOLOGIES).

—Probe—

The probe includes a probe consisting of a base sequence set forth in SEQ ID NO: 1 described below or a probe consisting of a complementary base sequence thereof and at least one of a probe consisting of a base sequence set forth in SEQ ID NO: 2 described below or a probe consisting of a complementary base sequence thereof, and a probe consisting of a base sequence set forth in SEQ ID NO: 18 described below or a probe consisting of a complementary base sequence thereof; and, if necessary, further includes other probes.

A sequence adjacent to a base sequence coding for the amino acid at position 93 of the HCV NS5A protein is set forth in the following SEQ ID NO: 13:

```
                                        (SEQ ID NO: 13)
       5'-aa(y)gc(n)ya(y)-3'.
```

SEQ ID NO: 13 is a sequence corresponding to a region coding for amino acids at positions 91 to 93 of the NS5A protein, and the underlined part corresponds to a region coding for the amino acid at position 93. In SEQ ID NO: 13, "y" denotes thymine or cytosine, and "n" denotes adenine, guanine, cytosine, or thymine.

As described in Production Example 1 described below, the mutation in the amino acid at position 93 of the NS5A protein is mainly caused by substituting the base t at position 277 with the base c. There is a variation between HCVs at bases at positions 273, 276, and 279 (bases described in parentheses in the SEQ ID NO: 13). Therefore, probe design is very important in order to quantitatively measure the presence or absence of the mutation in the amino acid at position 93 of the NS5A protein, at a low cost, easily, conveniently, and rapidly.

——Probe Consisting of Base Sequence Set Forth in SEQ ID NO: 1 or Probe Consisting of Complementary Base Sequence Thereof——

The probe consisting of a base sequence set forth in SEQ ID NO: 1 (hereinafter may be referred to as "Ycac type") has the following sequence:

```
(SEQ ID NO: 1)
5'-aacgcat[a]ca-3'.
```

In the SEQ ID NO: 1, the base a described in brackets denotes RNA and the underlined part denotes a sequence corresponding to the region coding for the amino acid at position 93 of the NS5A protein. The probe consisting of a base sequence set forth in SEQ ID NO: 1 has a sequence in which the amino acid at position 93 of the NS5A is tyrosine and bases described in parentheses in the base sequence set forth in SEQ ID NO: 13 are cac from the 5'-side.

The probe consisting of a base sequence set forth in SEQ ID NO: 1 does not include an RNA base at position 277, which causes the mutation in the amino acid at position 93 of the NS5A protein, but at position 278 adjacent thereto, so that an Ycgc type sequence (sequence in which the bases described in parentheses in the base sequence set forth in SEQ ID NO: 13 are cgc from the 5'-side), an Yccc type sequence (sequence in which the bases described in parentheses in the base sequence set forth in SEQ ID NO: 13 are ccc from the 5'-side), and an Yctc type sequence (sequence in which the bases described in parentheses in the base sequence set forth in SEQ ID NO: 13 are etc from the 5'-side) can be detected in addition to the Ycac type sequence. That is, it can be determined whether the amino acid at position 93 of the NS5A is tyrosine and an amount thereof without being affected by variation at "n" in the base sequence set forth in SEQ ID NO: 13.

The probe consisting of a base sequence set forth in SEQ ID NO: 1 may be the probe consisting of a complementary base sequence thereof.

The probe consisting of a base sequence set forth in SEQ ID NO: 1 or the probe consisting of a complementary base sequence thereof may be used alone or in combination. Among them, the probe consisting of a base sequence set forth in SEQ ID NO: 1 is preferable.

——Probe Consisting of Base Sequence Set Forth in SEQ ID NO: 2 or Probe Consisting of Complementary Base Sequence Thereof——

The probe consisting of a base sequence set forth in SEQ ID NO: 2 (hereinafter may be referred to as "Hcac type") has the following sequence:

```
(SEQ ID NO: 2)
5'-aacgcac[a]ca-3'.
```

In the SEQ ID NO: 2, the base a described in brackets denotes RNA and the underlined part denotes a sequence corresponding to the region coding for the amino acid at position 93 of the NS5A protein. The probe consisting of a base sequence set forth in SEQ ID NO: 2 has a sequence in which the amino acid at position 93 of the NS5A is histidine and the bases described in parentheses in the base sequence set forth in SEQ ID NO: 13 are cac from the 5'-side.

The probe consisting of a base sequence set forth in SEQ ID NO: 2 does not include an RNA base at position 277, which causes the mutation in the amino acid at position 93 of the NS5A protein, but at position 278 adjacent thereto, so that an Hcgc type sequence (sequence in which the bases described in parentheses in the base sequence set forth in SEQ ID NO: 13 are cgc from the 5'-side), an Hccc type sequence (sequence in which the bases described in parentheses in the base sequence set forth in SEQ ID NO: 13 are ccc from the 5'-side), and an Hctc type sequence (sequence in which the bases described in parentheses in the base sequence set forth in SEQ ID NO: 13 are ctc from the 5'-side, can be detected in addition to the Hcac type sequence. That is, it can be determined whether the amino acid at position 93 of the NS5A is histidine and an amount thereof without being affected by variation at "n" in the base sequence set forth in SEQ ID NO: 13.

The probe consisting of a base sequence set forth in SEQ ID NO: 2 may be the probe consisting of a complementary base sequence thereof.

——Probe Consisting of Base Sequence Set Forth in SEQ ID NO: 18 or Probe Consisting of Complementary Base Sequence Thereof——

The probe consisting of a base sequence set forth in SEQ ID NO: 18 (hereinafter may be referred to as "Hcac type") has the following sequence:

```
(SEQ ID NO: 18)
5'-acgcac[a]ca-3'.
```

In the SEQ ID NO: 18, the base a described in brackets denotes RNA and the underlined part denotes a sequence corresponding to the region coding for the amino acid at position 93 of the NS5A protein. The probe consisting of a base sequence set forth in SEQ ID NO: 18 has a sequence in which the amino acid at position 93 of the NS5A is histidine and the bases described in parentheses in the base sequence set forth in SEQ ID NO: 13 are cac from the 5'-side.

The probe consisting of a base sequence set forth in SEQ ID NO: 18 does not include an RNA base at position 277, which causes the mutation in the amino acid at position 93 of the NS5A protein, but at position 278 adjacent thereto, so that an Hcgc type sequence (sequence in which the bases described in parentheses in the base sequence set forth in SEQ ID NO: 13 are cgc from the 5'-side), an Hccc type sequence (sequence in which the bases described in parentheses in the base sequence set forth in SEQ ID NO: 13 are ccc from the 5'-side), and an Hctc type sequence (sequence in which the bases described in parentheses in the base sequence set forth in SEQ ID NO: 13 are etc from the 5'-side) can be detected in addition to the Hcac type sequence. That is, it can be determined whether the amino acid at position 93 of the NS5A is histidine and an amount thereof without being affected by variation at "n" in the base sequence set forth in SEQ ID NO: 13.

The probe consisting of a base sequence set forth in SEQ ID NO: 18 may be the probe consisting of a complementary base sequence thereof.

The probe consisting of a base sequence set forth in SEQ ID NO: 2 or the probe consisting of a complementary base sequence thereof, and the probe consisting of a base sequence set forth in SEQ ID NO: 18 or the probe consisting of a complementary base sequence thereof may be used alone or in combination. Among them, the probe consisting of a base sequence set forth in SEQ ID NO: 2 or the probe consisting of a base sequence set forth in SEQ ID NO: 18 is preferable.

——Other Probes——

The other probes are not particularly limited and may be appropriately selected depending on the intended purpose, so long as they do not impair the effects of the present invention.

A preferable aspect of the other probes includes a probe consisting of a base sequence set forth in SEQ ID NO: 9 described below or a probe consisting of a complementary base sequence thereof; and at least one of a probe consisting of a base sequence set forth in SEQ ID NO: 10 described below or a probe consisting of a complementary base sequence thereof, and a probe consisting of a base sequence set forth in SEQ ID NO: 22 described below or a probe consisting of a complementary base sequence thereof because the presence or absence of the mutation in the amino acid at position 93 of the hepatitis C virus NS5A protein can be detected at a higher accuracy.

——Probe Consisting of Base Sequence Set Forth in SEQ ID NO: 9 or Probe Consisting of Complementary Base Sequence Thereof——

The probe consisting of a base sequence set forth in SEQ ID NO: 9 (hereinafter may be referred to as "Ycgc type") has the following sequence:

(SEQ ID NO: 9)
5'-aacgcgt[a]ca-3'.

In the SEQ ID NO: 9, the base a described in brackets denotes RNA and the underlined part denotes a sequence corresponding to the region coding for the amino acid at position 93 of the NS5A protein. The probe consisting of a base sequence set forth in SEQ ID NO: 9 has a sequence in which the amino acid at position 93 of the NS5A is tyrosine and the bases described in parentheses in the base sequence set forth in SEQ ID NO: 13 are cgc from the 5'-side.

The probe consisting of a base sequence set forth in SEQ ID NO: 9 may be the probe consisting of a complementary base sequence thereof.

The probe consisting of a base sequence set forth in SEQ ID NO: 9 or the probe consisting of a complementary base sequence thereof may be used alone or in combination. Among them, the probe consisting of a base sequence set forth in SEQ ID NO: 9 is preferable.

When the probe consisting of a base sequence set forth in SEQ ID NO: 1 or the probe consisting of a complementary base sequence thereof is used in combination with the probe consisting of a base sequence set forth in SEQ ID NO: 9 or the probe consisting of a complementary base sequence thereof, a ratio of amounts used is not particularly limited and may be appropriately selected depending on the intended purpose. For example, they may be used at a ratio of 1:1 by number of molecules.

——Probe Consisting of Base Sequence Set Forth in SEQ ID NO: 10 or Probe Consisting of Complementary Base Sequence Thereof——

The probe consisting of a base sequence set forth in SEQ ID NO: 10 (hereinafter may be referred to as "Hcgc type") has the following sequence:

(SEQ ID NO: 10)
5'-aacgcgc[a]ca-3'.

In the SEQ ID NO: 10, the base a described in brackets denotes RNA and the underlined part denotes a sequence corresponding to the region coding for the amino acid at position 93 of the NS5A protein. The probe consisting of a base sequence set forth in SEQ ID NO: 10 has a sequence in which the amino acid at position 93 of the NS5A is histidine and the bases described in parentheses in the base sequence set forth in SEQ ID NO: 13 are cgc from the 5'-side.

The probe consisting of a base sequence set forth in SEQ ID NO: 10 may be the probe consisting of a complementary base sequence thereof.

——Probe Consisting of Base Sequence Set Forth in SEQ ID NO: 22 or Probe Consisting of Complementary Base Sequence Thereof——

The probe consisting of a base sequence set forth in SEQ ID NO: 22 (hereinafter may be referred to as "Hcgc type") has the following sequence:

(SEQ ID NO: 22)
5'-acgcgc[a]ca-3'.

In the SEQ ID NO: 22, the base a described in brackets denotes RNA and the underlined part denotes a sequence corresponding to the region coding for the amino acid at position 93 of the NS5A protein. The probe consisting of a base sequence set forth in SEQ ID NO: 22 has a sequence in which the amino acid at position 93 of the NS5A is histidine and the bases described in parentheses in the base sequence set forth in SEQ ID NO: 13 are cgc from the 5'-side.

The probe consisting of a base sequence set forth in SEQ ID NO: 22 may be the probe consisting of a complementary base sequence thereof.

The probe consisting of a base sequence set forth in SEQ ID NO: 10 or the probe consisting of a complementary base sequence thereof, and the probe consisting of a base sequence set forth in SEQ ID NO: 22 or the probe consisting of a complementary base sequence thereof may be used alone or in combination. Among them, the probe consisting of a base sequence set forth in SEQ ID NO: 10 or the probe consisting of a base sequence set forth in SEQ ID NO: 22 is preferable.

When at least one of the probe consisting of a base sequence set forth in SEQ ID NO: 2 or the probe consisting of a complementary base sequence thereof and the probe consisting of a base sequence set forth in SEQ ID NO: 18 or the probe consisting of a complementary base sequence thereof is used in combination with at least one of the probe consisting of a base sequence set forth in SEQ ID NO: 10 or the probe consisting of a complementary base sequence thereof and the probe consisting of a base sequence set forth in SEQ ID NO: 22 or the probe consisting of a complementary base sequence thereof, a ratio of amounts used is not particularly limited and may be appropriately selected depending on the intended purpose. For example, they may be used at a ratio of 1:1 by number of molecules.

The other probes may further include a probe consisting of a base sequence set forth in SEQ ID NO: 3 described below or a probe consisting of a complementary base sequence thereof; and at least one of a probe consisting of a base sequence set forth in SEQ ID NO: 4 described below or a probe consisting of a complementary base sequence thereof and a probe consisting of a base sequence set forth in SEQ ID NO: 19 described below or a probe consisting of a complementary base sequence thereof. The other probes may further include at least one of (1) a combination consisting of: a probe consisting of a base sequence set forth in SEQ ID NO: 5 described below or a probe consisting of a complementary base sequence thereof; and at least one of a probe consisting of a base sequence set forth in SEQ ID NO: 6 described below or a probe consisting of a complementary base sequence thereof and a probe consisting of a base sequence set forth in SEQ ID NO: 20 described below or a probe consisting of a complementary base sequence thereof; and (2) a combination Cconsisting of a probe consisting of: a base sequence set forth in SEQ ID NO: 7 described below or a probe consisting of a complementary base sequence thereof; and at least one of a probe consisting of a base sequence set forth in SEQ ID NO: 8 described below or a probe consisting of a complementary base sequence thereof and a probe consisting of a base sequence set forth in SEQ ID NO: 21 described below or a probe consisting of a complementary base sequence thereof.

The other probes can be used to detect the mutation in the amino acid at position 93 of the hepatitis C virus NS5A protein in much more samples.

———Probe Consisting of Base Sequence Set Forth in SEQ ID NO: 3 or Probe Consisting of Complementary Base Sequence Thereof———

The probe consisting of a base sequence set forth in SEQ ID NO: 3 (hereinafter may be referred to as "Ycat type") has the following sequence:

(SEQ ID NO: 3)
5'-aacgcat[a]ta-3'.

In the SEQ ID NO: 3, the base a described in brackets denotes RNA and the underlined part denotes a sequence corresponding to the region coding for the amino acid at position 93 of the NS5A protein. The probe consisting of a base sequence set forth in SEQ ID NO: 3 has a sequence in which the amino acid at position 93 of the NS5A is tyrosine and the bases described in parentheses in the base sequence set forth in SEQ ID NO: 13 are cat from the 5'-side.

The probe consisting of a base sequence set forth in SEQ ID NO: 3 may be the probe consisting of a complementary base sequence thereof.

The probe consisting of a base sequence set forth in SEQ ID NO: 3 or the probe consisting of a complementary base sequence thereof may be used alone or in combination. Among them, the probe consisting of a base sequence set forth in SEQ ID NO: 3 is preferable.

———Probe Consisting of Base Sequence Set Forth in SEQ ID NO: 4 or Probe Consisting of Complementary Base Sequence Thereof———

The probe consisting of a base sequence set forth in SEQ ID NO: 4 (hereinafter may be referred to as "Hcat type") has the following sequence:

(SEQ ID NO: 4)
5'-aacgcac[a]ta-3'.

In the SEQ ID NO: 4, the base a described in brackets denotes RNA and the underlined part denotes a sequence corresponding to the region coding for the amino acid at position 93 of the NS5A protein. The probe consisting of a base sequence set forth in SEQ ID NO: 4 has a sequence in which the amino acid at position 93 of the NS5A is histidine and the bases described in parentheses in the base sequence set forth in SEQ ID NO: 13 are cat from the 5'-side.

The probe consisting of a base sequence set forth in SEQ ID NO: 4 may be the probe consisting of a complementary base sequence thereof.

———Probe Consisting of Base Sequence Set Forth in SEQ ID NO: 19 or Probe Consisting of Complementary Base Sequence Thereof———

The probe consisting of a base sequence set forth in SEQ ID NO: 19 (hereinafter may be referred to as "Heat type") has the following sequence:

(SEQ ID NO: 19)
5'-acgcac[a]ta-3'.

In the SEQ ID NO: 19, the base a described in brackets denotes RNA and the underlined part denotes a sequence corresponding to the region coding for the amino acid at position 93 of the NS5A protein. The probe consisting of a base sequence set forth in SEQ ID NO: 19 has a sequence in which the amino acid at position 93 of the NS5A is histidine and the bases described in parentheses in the base sequence set forth in SEQ ID NO: 13 are cat from the 5'-side.

The probe consisting of a base sequence set forth in SEQ ID NO: 19 may be the probe consisting of a complementary base sequence thereof.

The probe consisting of a base sequence set forth in SEQ ID NO: 4 or the probe consisting of a complementary base sequence thereof and the probe consisting of a base sequence set forth in SEQ ID NO: 19 or the probe consisting of a complementary base sequence thereof may be used alone or in combination. Among them, the probe consisting of a base sequence set forth in SEQ ID NO: 4 or the probe consisting of a base sequence set forth in SEQ ID NO: 19 is preferable.

———Probe Consisting of Base Sequence Set Forth in SEQ ID NO: 5 or Probe Consisting of Complementary Base Sequence Thereof———

The probe consisting of a base sequence set forth in SEQ ID NO: 5 (hereinafter may be referred to as "Ytac type") has the following sequence:

(SEQ ID NO: 5)
5'-aatgcat[a]ca-3'.

In the SEQ ID NO: 5, the base a described in brackets denotes RNA and the underlined part denotes a sequence corresponding to the region coding for the amino acid at position 93 of the NS5A protein. The probe consisting of a base sequence set forth in SEQ ID NO: 5 has a sequence in which the amino acid at position 93 of the NS5A is tyrosine and the bases described in parentheses in the base sequence set forth in SEQ ID NO: 13 are tac from the 5'-side.

The probe consisting of a base sequence set forth in SEQ ID NO: 5 may be the probe consisting of a complementary base sequence thereof.

The probe consisting of a base sequence set forth in SEQ ID NO: 5 or the probe consisting of a complementary base sequence thereof may be used alone or in combination. Among them, the probe consisting of a base sequence set forth in SEQ ID NO: 5 is preferable.

——Probe Consisting of Base Sequence Set Forth in SEQ ID NO: 6 or Probe Consisting of Complementary Base Sequence Thereof——

The probe consisting of a base sequence set forth in SEQ ID NO: 6 (hereinafter may be referred to as "Htac type") has the following sequence:

(SEQ ID NO: 6)
5'-aatgcac[a]ca-3'.

In the SEQ ID NO: 6, the base a described in brackets denotes RNA and the underlined part denotes a sequence corresponding to the region coding for the amino acid at position 93 of the NS5A protein. The probe consisting of a base sequence set forth in SEQ ID NO: 6 has a sequence in which the amino acid at position 93 of the NS5A is histidine and the bases described in parentheses in the base sequence set forth in SEQ ID NO: 13 are tac from the 5'-side.

The probe consisting of a base sequence set forth in SEQ ID NO: 6 may be the probe consisting of a complementary base sequence thereof.

——Probe Consisting of Base Sequence Set Forth in SEQ ID NO: 20 or Probe Consisting of Complementary Base Sequence Thereof——

The probe consisting of a base sequence set forth in SEQ ID NO: 20 (hereinafter may be referred to as "Htac type") has the following sequence:

(SEQ ID NO: 20)
5'-atgcac[a]ca-3'.

In the SEQ ID NO: 20, the base a described in brackets denotes RNA and the underlined part denotes a sequence corresponding to the region coding for the amino acid at position 93 of the NS5A protein. The probe consisting of a base sequence set forth in SEQ ID NO: 20 has a sequence in which the amino acid at position 93 of the NS5A is histidine and the bases described in parentheses in the base sequence set forth in SEQ ID NO: 13 are tac from the 5'-side.

The probe consisting of a base sequence set forth in SEQ ID NO: 20 may be the probe consisting of a complementary base sequence thereof.

The probe consisting of a base sequence set forth in SEQ ID NO: 6 or probe consisting of a complementary base sequence thereof and the probe consisting of a base sequence set forth in SEQ ID NO: 20 or the probe consisting of a complementary base sequence thereof may be used alone or in combination. Among them, the probe consisting of a base sequence set forth in SEQ ID NO: 6 or the probe consisting of a base sequence set forth in SEQ ID NO: 20 is preferable.

——Probe Consisting of Base Sequence Set Forth in SEQ ID NO: 7 or Probe Consisting of Complementary Base Sequence Thereof——

The probe consisting of a base sequence set forth in SEQ ID NO: 7 (hereinafter may be referred to as "Ytat type") has the following sequence:

(SEQ ID NO: 7)
5'-aatgcat[a]ta-3'.

In the SEQ ID NO: 7, the base a described in brackets denotes RNA and the underlined part denotes a sequence corresponding to the region coding for the amino acid at position 93 of the NS5A protein. The probe consisting of a base sequence set forth in SEQ ID NO: 7 has a sequence in which the amino acid at position 93 of the NS5A is tyrosine and the bases described in parentheses in the base sequence set forth in SEQ ID NO: 13 are tat from the 5'-side.

The probe consisting of a base sequence set forth in SEQ ID NO: 7 may be the probe consisting of a complementary base sequence thereof.

The probe consisting of a base sequence set forth in SEQ ID NO: 7 or the probe consisting of a complementary base sequence thereof may be used alone or in combination. Among them, the probe consisting of a base sequence set forth in SEQ ID NO: 7 is preferable.

——Probe Consisting of Base Sequence Set Forth in SEQ ID NO: 8 or Probe Consisting of Complementary Base Sequence Thereof——

The probe consisting of a base sequence set forth in SEQ ID NO: 8 (hereinafter may be referred to as "Htat type") has the following sequence:

(SEQ ID NO: 8)
5'-aatgcac[a]ta-3'.

In the SEQ ID NO: 8, the base a described in brackets denotes RNA and the underlined part denotes a sequence corresponding to the region coding for the amino acid at position 93 of the NS5A protein. The probe consisting of a base sequence set forth in SEQ ID NO: 8 has a sequence in which the amino acid at position 93 of the NS5A is histidine and the bases described in parentheses in the base sequence set forth in SEQ ID NO: 13 are tat from the 5'-side.

The probe consisting of a base sequence set forth in SEQ ID NO: 8 may be the probe consisting of a complementary base sequence thereof.

——Probe Consisting of Base Sequence Set Forth in SEQ ID NO: 21 or Probe Consisting of Complementary Base Sequence Thereof——

The probe consisting of a base sequence set forth in SEQ ID NO: 21 (hereinafter may be referred to as "Htat type") has the following sequence:

(SEQ ID NO: 21)
5'-atgcac[a]ta-3'.

In the SEQ ID NO: 21, the base a described in brackets denotes RNA and the underlined part denotes a sequence corresponding to the region coding for the amino acid at position 93 of the NS5A protein. The probe consisting of a base sequence set forth in SEQ ID NO: 21 has a sequence in which the amino acid at position 93 of the NS5A is histidine and the bases described in parentheses in the base sequence set forth in SEQ ID NO: 13 are tat from the 5'-side.

The probe consisting of a base sequence set forth in SEQ ID NO: 21 may be the probe consisting of a complementary base sequence thereof.

The probe consisting of a base sequence set forth in SEQ ID NO: 8 or the probe consisting of a complementary base sequence thereof and the probe consisting of a base sequence set forth in SEQ ID NO: 21 or the probe consisting of a complementary base sequence thereof may be used alone or in combination. Among them, the probe consisting of a base sequence set forth in SEQ ID NO: 8 or the probe consisting of a base sequence set forth in SEQ ID NO: 21 is preferable.

In the real-time PCR, with the cycling probe method, the following combination (1) is used as the probe; and, if necessary, at least one of the following combinations (2), (3), (4), and (5) is further used. Among them, an aspect including the following combinations (1) and (2) is preferable.

(1) a combination of the probe consisting of a base sequence set forth in SEQ ID NO: 1 or the probe consisting of a complementary base sequence thereof; and at least one of the probe consisting of a base sequence set forth in SEQ ID NO: 2 or the probe consisting of a complementary base sequence thereof, and the probe consisting of a base sequence set forth in SEQ ID NO: 18 or the probe consisting of a complementary base sequence thereof.

(2) a combination of the probe consisting of a base sequence set forth in SEQ ID NO: 9 or the probe consisting of a complementary base sequence thereof; and at least one of the probe consisting of a base sequence set forth in SEQ ID NO: 10 or the probe consisting of a complementary base sequence thereof, and the probe consisting of a base sequence set forth in SEQ ID NO: 22 or the probe consisting of a complementary base sequence thereof.

(3) a combination of the probe consisting of a base sequence set forth in SEQ ID NO: 3 or the probe consisting of a complementary base sequence thereof; and at least one of the probe consisting of a base sequence set forth in SEQ ID NO: 4 or the probe consisting of a complementary base sequence thereof, and the probe consisting of a base sequence set forth in SEQ ID NO: 19 or the probe consisting of a complementary base sequence thereof.

(4) a combination of the probe consisting of a base sequence set forth in SEQ ID NO: 5 or the probe consisting of a complementary base sequence thereof; and at least one of the probe consisting of a base sequence set forth in SEQ ID NO: 6 or the probe consisting of a complementary base sequence thereof, and the probe consisting of a base sequence set forth in SEQ ID NO: 20 or the probe consisting of a complementary base sequence thereof.

(5) a combination of the probe consisting of a base sequence set forth in SEQ ID NO: 7 or the probe consisting of a complementary base sequence thereof; and at least one of the probe consisting of a base sequence set forth in SEQ ID NO: 8 or the probe consisting of a complementary base sequence thereof, and the probe consisting of a base sequence set forth in SEQ ID NO: 21 or the probe consisting of a complementary base sequence thereof.

—Primer Set—

The primer set is not particularly limited and may be appropriately selected depending on the intended purpose, so long as it is a primer set which is designed to be able to amplify a region including the base sequence coding for the amino acid at position 93 of the hepatitis C virus NS5A protein. However, the primer set is preferably a primer set consisting of a primer consisting of a base sequence set forth in SEQ ID NO: 11 described below and a primer consisting of a base sequence set birth in SEQ ID NO: 12 described below or a primer set consisting of a primer consisting of a base sequence complementary to SEQ ID NO: 11 described below and a primer consisting of a base sequence complementary to SEQ ID NO: 12 described below because the region including the base sequence coding for the amino acid at position 93 of various HCV NS5A protein s in a sample can be amplified.

——Primer Consisting of Base Sequence Set Forth in SEQ ID NO: 11 or Primer Consisting of Complementary Base Sequence Thereof——

The primer consisting of a base sequence set forth in SEQ ID NO: 11 corresponds to bases at positions 208 to 226 in the base sequence coding for the NS5A protein and has the following sequence:

(SEQ ID NO: 11)
5'-ggttccatgaggatcgttg-3'.

The primer consisting of a base sequence set forth in SEQ ID NO: 11 may be the primer consisting of a complementary base sequence thereof, but the primer consisting of a base sequence set forth in SEQ ID NO: 11 is preferable.

——Primer Consisting of Base Sequence Set Forth in SEQ ID NO: 12 or Primer Consisting of Complementary Base Sequence Thereof——

The primer consisting of a base sequence set forth in SEQ ID NO: 12 corresponds to bases at positions 376 to 394 in the base sequence coding for the NS5A protein and has the following sequence:

(SEQ ID NO: 12)
5'-ccgtcacgtagtggaaatc-3'.

The primer consisting of a base sequence set forth in SEQ ID NO: 12 may be the primer consisting of a complementary base sequence thereof, but the primer consisting of a base sequence set forth in SEQ ID NO: 12 is preferable.

The real-time PCR may be performed in a single reactor containing the combination of probes or may be performed in separate reactors each containing the probe. However, the real-time PCR is preferably performed in the separate reactors from the viewpoint of excellent detection sensitivity.

When the real-time PCR is performed in the single reactor containing the combination of probes, the probes may be modified with different fluorescent substances. When the real-time PCR is performed in the separate reactors each containing the probe, the probes may be modified with a single fluorescent substance or different fluorescent substances.

The real-time PCR may be performed with CYCLEAVE (registered trademark) PCR REACTION MIX (product of Takara Bio Inc.).

A reaction condition of the real-time PCR is not particularly limited and may be appropriately selected depending on the intended purpose.

The real-time PCR enables the presence or absence of the mutation in the amino acid at position 93 of the HCV NS5A protein in the sample to be quantitatively measured, and the mutation in the amino acid at position 93 of the HCV NS5A protein to be detected.

<Other Steps>

The other steps are not particularly limited and may be appropriately selected depending on the intended purpose, so long as they do not impair the effects of the present invention. An example thereof includes a collecting step which is a step of collecting blood or a tissue from the subject.

(Kit for Detecting Mutation in Amino Acid at Position 93 of Hepatitis C Virus NS5A Protein)

A kit for detecting the HCV NS5A Y93 mutation according to the present invention includes the probe consisting of a base sequence set forth in SEQ ID NO: 1 or the probe consisting of a complementary base sequence thereof; and at least one of the probe consisting of a base sequence set forth in SEQ ID NO: 2 or the probe consisting of a complementary base sequence thereof, and the probe consisting of a base sequence set forth in SEQ ID NO: 18 or the probe consisting of a complementary base sequence thereof; and, if necessary, further includes other components.

A genotype of the hepatitis C virus is not particularly limited and may be appropriately selected depending on the intended purpose, but is preferably type 1a, type 1b, type 2a, and type 2b.

<Probe Consisting of Base Sequence Set Forth in SEQ ID NO: 1 or Probe Consisting of Complementary Base Sequence Thereof>

The probe consisting of a base sequence set forth in SEQ ID NO: 1 or the probe consisting of a complementary base sequence thereof is the same as described under the heading "Probe consisting of base sequence set forth in SEQ ID NO: 1 or probe consisting of complementary base sequence thereof" with respect to the method for detecting a HCV NS5A Y93 mutation according to the present invention. The same is applied to a preferable aspect thereof.

<Probe Consisting of Base Sequence Set Forth in SEQ ID NO: 2 or Probe Consisting of Complementary Base Sequence Thereof>

The probe consisting of a base sequence set forth in SEQ ID NO: 2 or the probe consisting of a complementary base sequence thereof is the same as described under the heading "Probe consisting of base sequence set forth in SEQ ID NO: 2 or probe consisting of complementary base sequence thereof" with respect to the method for detecting a HCV NS5A Y93 mutation according to the present invention. The same is applied to a preferable aspect thereof.

<Probe Consisting of Base Sequence Set Forth in SEQ ID NO: 18 or Probe Consisting of Complementary Base Sequence Thereof>

The probe consisting of a base sequence set forth in SEQ ID NO: 18 or the probe consisting of a complementary base sequence thereof is the same as described under the heading "Probe consisting of base sequence set forth in SEQ ID NO: 18 or probe consisting of complementary base sequence thereof" with respect to the method for detecting a HCV NS5A Y93 mutation according to the present invention. The same is applied to a preferable aspect thereof.

<Other Components>

The other components are not particularly limited and may be appropriately selected depending on the intended purpose, so long as they do not impair the effects of the present invention. Example thereof include probes other than the probe consisting of a base sequence set forth in SEQ ID NO: 1 or the probe consisting of a complementary base sequence thereof, the probe consisting of a base sequence set forth in SEQ ID NO: 2 or the probe consisting of a complementary base sequence thereof, and the probe consisting of a base sequence set forth in SEQ ID NO: 18 or the probe consisting of a complementary base sequence thereof (hereinafter may be referred to as "other probes"), primer sets, and reagents used for PCR.

—Other Probes—

The other probes in the kit for detecting the HCV NS5A Y93 mutation are not particularly limited and may be appropriately selected depending on the intended purpose, so long as they do not impair the effects of the present invention.

A preferable aspect of the other probes includes a probe consisting of a base sequence set forth in SEQ ID NO: 9 described below or a probe consisting of a complementary base sequence thereof, and at least one of a probe consisting of a base sequence set forth in SEQ ID NO: 10 described below or a probe consisting of a complementary base sequence thereof, and a probe consisting of a base sequence set forth in SEQ ID NO: 22 described below or a probe consisting of a complementary base sequence thereof because the presence or absence of the mutation in the amino acid at position 93 of the hepatitis C virus NS5A protein can be detected at a higher accuracy.

——Probe Consisting of Base Sequence Set Forth in SEQ ID NO: 9 or Probe Consisting of Complementary Base Sequence Thereof——

The probe consisting of a base sequence set forth in SEQ ID NO: 9 or the probe consisting of a complementary base sequence thereof is the same as described under the heading "Probe consisting of base sequence set forth in SEQ ID NO: 9 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 10 or Probe Consisting of Complementary Base Sequence Thereof——

The probe consisting of a base sequence set forth in SEQ ID NO: 10 or the probe consisting of a complementary base sequence thereof is the same as described under the heading "Probe consisting of base sequence set forth in SEQ ID NO: 10 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 22 or Probe Consisting of Complementary Base Sequence Thereof——

The probe consisting of a base sequence set forth in SEQ ID NO: 22 or the probe consisting of a complementary base sequence thereof is the same as described under the heading "Probe consisting of base sequence set forth in SEQ ID NO: 22 or probe consisting of complementary base sequence thereof" with respect to the method for detecting a HCV NS5A Y93 mutation according to the present invention. The same is applied to a preferable aspect thereof.

The other probes may further include a probe consisting of a base sequence set forth in SEQ ID NO: 3 described below or a probe consisting of a complementary base sequence thereof; and at least one of a probe consisting of a base sequence set forth in SEQ ID NO: 4 described below or a probe consisting of a complementary base sequence thereof and a probe consisting of a base sequence set forth in SEQ ID NO: 19 described below or a probe consisting of a complementary base sequence thereof. The other probes may further include at least one of (1) a combination consisting of: a probe consisting of a base sequence set forth, in SEQ ID NO: 5 described below or a probe consisting of a complementary base sequence thereof, and at least one of a probe consisting of a base sequence set forth in SEQ ID NO: 6 described below or a probe consisting of a complementary base sequence thereof and a probe consisting of a base sequence set forth in SEQ ID NO: 20 described below or a probe consisting of a complementary base sequence thereof; and (2) a combination consisting of: a probe consisting of a base sequence set forth in SEQ ID NO: 7 described below or a probe consisting of a complementary base sequence thereof; and, at least one of a probe consisting of a base sequence set forth in SEQ ID NO: 8 described below or a probe consisting of a complementary base sequence thereof and a probe consisting of a base sequence set forth in SEQ ID NO: 21 described below or a probe consisting of a complementary base sequence thereof.

The other probes can be used to detect the mutation in the amino acid at position 93 of the hepatitis C virus NS5A protein in much, more samples.

——Probe Consisting of Base Sequence Set Forth in SEQ ID NO: 3 or Probe Consisting of Complementary Base Sequence Thereof——

The probe consisting of a base sequence set forth in SEQ ID NO: 3 or the probe consisting of a complementary base sequence thereof is the same as described under the heading "Probe consisting of base sequence set forth in SEQ ID NO: 3 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 4 or Probe Consisting of Complementary Base Sequence Thereof——

The probe consisting of a base sequence set forth in SEQ ID NO: 4 or the probe consisting of a complementary base sequence thereof is the same as described under the heading "Probe consisting of base sequence set forth in SEQ ID NO: 4 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 19 or Probe Consisting of Complementary Base Sequence Thereof——

The probe consisting of a base sequence set forth in SEQ ID NO: 19 or the probe consisting of a complementary base sequence thereof is the same as described under the heading "Probe consisting of base sequence set forth in SEQ ID NO: 19 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 5 or Probe Consisting of Complementary Base Sequence Thereof——

The probe consisting of a base sequence set forth in SEQ ID NO: 5 or the probe consisting of a complementary base sequence thereof is the same as described under the heading "Probe consisting of base sequence set forth in SEQ ID NO: 5 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 6 or Probe Consisting of Complementary Base Sequence Thereof——

The probe consisting of a base sequence set forth in SEQ ID NO: 6 or the probe consisting of a complementary base sequence thereof is the same as described under the heading "Probe consisting of base sequence set forth in SEQ ID NO: 6 or probe consisting of complementary base sequence thereof" with respect, to the method for detecting HCV NS5A Y93 mutation according to the present invention. The same is applied to a preferable aspect thereof.

——Probe Consisting of Base Sequence Set Forth in SEQ ID NO: 20 or Probe Consisting of Complementary Base Sequence Thereof——

The probe consisting of a base sequence set forth in SEQ ID NO: 20 or the probe consisting of a complementary base sequence thereof is the same as described under the heading "Probe consisting of base sequence set forth in SEQ ID NO: 20 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 7 or Probe Consisting of Complementary Base Sequence Thereof——

The probe consisting of a base sequence set forth in SEQ ID NO: 7 or the probe consisting of a complementary base sequence thereof is the same as described under the heading "Probe consisting of base sequence set forth in SEQ ID NO: 7 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 8 or Probe Consisting of Complementary Base Sequence Thereof——

The probe consisting of a base sequence set forth in SEQ ID NO: 8 or the probe consisting of a complementary base sequence thereof is the same as described under the heading "Probe consisting of base sequence set forth in SEQ ID NO: 8 or probe consisting of complementary base sequence thereof" with respect to the method for detecting a HCV NS5A Y93 mutation according to the present invention. The same is applied to a preferable aspect thereof.

——Probe Consisting of Base Sequence Set Forth in SEQ ID NO: 21 or Probe Consisting of Complementary Base Sequence Thereof——

The probe consisting of a base sequence set forth in SEQ ID NO: 21 or the probe consisting of a complementary base sequence thereof is the same as described under the heading "Probe consisting of base sequence set forth in SEQ ID NO: 21 or probe consisting of complementary base sequence thereof" with respect to the method for detecting a HCV NS5A Y93 mutation according to the present invention. The same is applied to a preferable aspect thereof.

—Primer Set—

The primer set is not particularly limited and may be appropriately selected depending on the intended purpose, so long as it is a primer set which is designed to be able to amplify the region including the base sequence coding for the amino acid at position 93 of the hepatitis C virus NS5A protein. However, the primer set is preferably a primer set consisting of a primer consisting of a base sequence set forth in SEQ ID NO: 11 described below and a primer consisting of a base sequence set forth in SEQ ID NO: 12 described below or a primer set consisting of a primer consisting of a base sequence complementary to SEQ ID NO: 11 described below and a primer consisting of a base sequence complementary to SEQ ID NO: 12 described below because the region including the base sequence coding for the amino acid at position 93 of various HCV NS5A proteins in a sample can be amplified.

——Primer Consisting of a Base Sequence Set Forth in SEQ ID NO: 11 or Primer Consisting of Complementary Base Sequence Thereof——

The primer consisting of a base sequence set forth in SEQ ID NO: 11 or the primer consisting of a complementary base sequence thereof is the same as described under the heading "Primer consisting of base sequence set forth in SEQ ID NO: 11 or primer consisting of complementary base sequence thereof" with respect to the method for detecting a HCV NS5A Y93 mutation according to the present invention. The same is applied to a preferable aspect thereof.

——Primer Consisting of a Base Sequence Set Forth in SEQ ID NO: 12 or Primer Consisting of Complementary Base Sequence Thereof——

The primer consisting of a base sequence set forth in SEQ ID NO: 12 or the primer consisting of a complementary base sequence thereof is the same as described under the heading "Primer consisting of base sequence set forth in SEQ ID NO: 12 or primer consisting of complementary base sequence thereof" with respect to the method for detecting a HCV NS5A Y93 mutation according to the present invention. The same is applied to a preferable aspect thereof.

EXAMPLES

The present invention will now be described with reference to Production Examples and Test Examples, but the present invention is not limited to Production Examples and Test Examples in any way.

Production Example 1: Probe

<Probe Design>

Base sequences of 647 HCVs registered to public DNA databases were examined. The examination result of a base sequence adjacent to a base sequence coding for an amino acid at position 93 (wild type: tyrosine) of an NS5A protein is presented in Table 1. Note that, the base sequence adjacent to the base sequence coding for the amino acid at position 93 of the NS5A protein was as set forth in the following SEQ ID NO: 13:

(SEQ ID NO: 13)
5'-aa(y)gc(n)ya(y)-3'.

SEQ ID NO: 13 is a sequence corresponding to a region coding for amino acids at positions 91 to 93 of the NS5A protein, and the underlined part corresponds to a region coding for the amino acid at position 93. In SEQ ID NO: 13, "y" denotes thymine or cytosine, and "n" denotes adenine, guanine, cytosine, or thymine.

TABLE 1

| | | Base sequence | | | | | | | |
|---|---|---|---|---|---|---|---|---|---|
| Base | | a | a | y | g | c | n | y | a | y |
| Base number | | 271 | 272 | 273 | 274 | 275 | 276 | 277 | 278 | 279 |
| Amino acid number | | | 91 | | | 92 | | | 93 | |
| Examination result | t | 0 | 0 | 33 | 0 | 0 | 311 | 609 | 0 | 13 |
| | c | 0 | 0 | 614 | 0 | 647 | 270 | 38 | 0 | 634 |
| | a | 647 | 647 | 0 | 0 | 0 | 62 | 0 | 647 | 0 |
| | g | 0 | 0 | 0 | 647 | 0 | 4 | 0 | 0 | 0 |

It can be seen from Table 1 that the mutation in the amino acid at position 93 of the NS5A protein is caused by mutation from t (277 nt) a (278 nt) c (279 nt) to cac through substitution of t at 277 nt with c.

In a cycling probe method, a position of mutation generally corresponds to an RNA moiety of a probe. Therefore, it was considered to design a probe in which the base at position 277 was RNA. However, as described, below in Test Example 5, it was found that when the base at position 277 was RNA, variation at the base at position 276 affected results of real-time PCR, so that probes corresponding to each of variations have to be prepared in order to detect HCVs with various variations.

Accordingly, a probe set as set forth in SEQ ID NOs: 1 and 2 in which the bases at position 278 adjacent to the position of mutation were RNA was designed.
—Probe Set—
Ycac Type-1:

(SEQ ID NO: 1)
5'-aacgcat[a]ca-3'

In SEQ ID NO: 1, the base a described in brackets denotes RNA, and the underlined part denotes a sequence corresponding to the region coding for the amino acid at position 93 of the NS5A protein. The Ycac type-1 had a sequence in which the amino acid at position 93 of the NS5A was tyrosine and the bases described in parentheses in the base sequence set forth in SEQ ID NO: 13 were cac from the 5'-side.

The Ycac type-1 probe was modified with a fluorescent substance (FAM) at the 5'-terminus and with a quenching substance (ECLIPSE DARK QUENCHER (product of Epoch Biosciences)) at the 3'-terminus.

Hcac Type-1:

(SEQ ID NO: 2)
5'-aacgcac[a]ca-3'

In SEQ ID NO: 2, the base a described in brackets denotes RNA, and the underlined part denotes a sequence corresponding to the region coding for the amino acid at position 93 of the NS5A protein. The Hcac type-1 had a sequence in which the amino acid at position 93 of the NS5A was histidine and the bases described in parentheses in the base sequence set forth in SEQ ID NO: 13 were cac from the 5'-side.

The Hcac type-1 probe was modified with a fluorescent substance (FAM) at the 5'-terminus and with a quenching substance (ECLIPSE DARK QUENCHER (product of Epoch Biosciences)) at the 3'-terminus.

Production Example 2: Primer

As a primer set which was designed to be able to amplify the region including the base sequence coding for the amino acid at position 93 of the hepatitis C virus NS5A protein, a primer set consisting of base sequences set forth in the following SEQ ID NOs: 11 and 12 was prepared. The primer set was designed by finding a region with high homology which can be used in the real-time PCR, based on base sequences of about 600 HCVs registered to public DNA databases.

HCV_Y93-1L:

(SEQ ID NO: 11)
5'-ggttccatgaggatcgtt-3'

The base sequence set forth in SEQ ID NO: 11 corresponded to bases at positions 208 to 226 in the base sequence coding for the NS5A protein.

HCV_Y93-1R:

(SEQ ID NO: 12)
5'-ccgtcacgtagtggaaatc-3'

The base sequence set forth in SEQ ID NO: 12 corresponded to bases at positions 376 to 394 in the base sequence coding for the NS5A protein.

Preparative Example 1: Artificial Synthetic Gene

The following artificial synthetic genes were prepared as artificial synthetic genes for verifying whether the mutation in the amino acid at position 93 of the hepatitis C virus NS5A protein can be detected by the real-time PCR using the probe designed in Production Example 1 or 3 and the primer designed in Production Example 2. Note that, the artificial synthetic genes were prepared with reference to the genomic RNA sequence of hepatitis C virus genotype 1b.

Artificial Synthetic Gene-1 (Wild-Type):

Double-stranded DNA consisting of a strand having a base sequence corresponding to bases at positions 198 to 404 in the base sequence coding for the NS5A protein in which the base sequence coding for the amino acids at positions 91 to 93 is “aacgcatac” (SEQ ID NO: 14) and a complementary strand thereof. Artificial synthetic gene-1 had a sequence in which the bases described in parentheses in the base sequence set forth in SEQ ID NO: 13 were cac from the 5'-side.

Artificial Synthetic Gene-2 (Mutated Form):

Double-stranded DNA consisting of a strand having a base sequence set forth in SEQ ID NO: 14 in which the base sequence coding for the amino acids at positions 91 to 93 of the NS5A protein is “aacgcacac” (SEQ ID NO: 15) and a complementary strand thereof. Artificial synthetic gene-2 had a sequence in which the bases described in parentheses in the base sequence set forth in SEQ ID NO: 13 were cac from the 5'-side.

Artificial Synthetic Gene-3 (Mutated Form):

Double-stranded DNA consisting of a strand having a base sequence set forth in SEQ ID NO: 14 in which the base sequence coding for the amino acids at positions 91 to 93 of the NS5A protein is “aacgcgtac” (SEQ ID NO: 16) and a complementary strand thereof. Artificial synthetic gene-3 had a sequence in which the bases described in parentheses in the base sequence set forth in SEQ ID NO: 13 were cgc from the 5'-side.

Artificial Synthetic Gene-4 (Wild-Type):

Double-stranded DNA consisting of a strand having a base sequence corresponding to bases at positions 198 to 404 in the base sequence coding for the NS5A protein in which the base sequence coding for the amino acids at positions 91 to 93 is “aacgcgtac” (SEQ ID NO: 23) and a complementary strand thereof. Artificial synthetic gene-4 had a sequence in which the bases described in parentheses in the base sequence set forth in SEQ ID NO: 13 were cgc from the 5'-side.

Test Example 1

<Preparation of Artificial Synthetic Gene Sample>

Artificial synthetic gene-1 (wild-type: Y93) and Artificial synthetic gene-2 (mutated form: Y93H) prepared in Preparative Example 1 were mixed as described in Table 2 to thereby prepare samples of artificial synthetic gene.

TABLE 2

| Sample name | Amount of artificial synthetic gene (number of molecules): Artificial synthetic gene-1 (Ycac) | Artificial synthetic gene-2 (Hcac) | Mixed ratio of Artificial synthetic gene-2 (%) |
|---|---|---|---|
| A-1 | $1.00 \times 10^6$ | 0 | 0 |
| B-1 | $9.50 \times 10^5$ | $5.00 \times 10^4$ | 5 |
| C-1 | $9.00 \times 10^5$ | $1.00 \times 10^5$ | 10 |
| D-1 | $7.00 \times 10^5$ | $3.00 \times 10^5$ | 30 |
| E-1 | $5.00 \times 10^5$ | $5.00 \times 10^5$ | 50 |
| F-1 | $3.00 \times 10^5$ | $7.00 \times 10^5$ | 70 |
| G-1 | $1.00 \times 10^5$ | $9.00 \times 10^5$ | 90 |
| H-1 | 0 | $1.00 \times 10^6$ | 100 |

<Real-Time PCR>

For each of samples A-1 to H-1, the real-time PCR (reaction device: Light Cycler 480) was performed in a reaction liquid having the composition described below (see, Table 3) using the probes designed in Production Example 1, the primer set designed in Production Example 2, and CYCLEAVE (registered trademark) PCR REACTION MIX (product of Takara Bio Inc.) under the reaction conditions described below.

Note that, in the real-time PCR, the Ycac type probe (SEQ ID NO: 1) and the Hcac type probe (SEQ ID NO: 2) were placed into different wells, where the reaction was performed.

—Reaction Condition—

——Hold (Initial Denaturation)——

Number of cycle: 1

Condition: at 95° C. for 30 sec

——3-Step PCR——

Number of cycle: 45

Condition: at 95° C. for 5 sec, at 55° C. for 10 sec, and then at 72° C. for 25 sec.

TABLE 3

<Per 1 reaction>

| Reagent | Used amount | Final concentration |
|---|---|---|
| Cycleave PCR Reaction Mix (2 × conc.) | 10 μL | 1× |
| PCR Forward Primer (10 μM) | 0.4 μL | 0.2 μM |
| PCR Reverse Primer (10 μM) | 0.4 μL | 0.2 μM |
| Cycling probe (5 μM) | 0.8 μL | 0.2 μM |
| ROX Reference Dye (50 × conc.) or Dye II (50 × conc.) | 0.4 μL | 1× |
| template (<100 ng) | 1.0 μL | |
| $dH_2O$ (sterile distilled water) | 7.0 μL | |
| total | 20 μL | |

From the results of the real-time PCR, the mutation in the amino acid at position 93 of the NS5A protein was quantified and a rate of mutation was calculated. Results are presented in Table 4.

TABLE 4

| Sample name | Measurement result Amino acid at position 93 | | | | Rate of mutation to Y93H in sample (%) |
|---|---|---|---|---|---|
| | Y | | H | | |
| | Copy number | Log value | Copy number | Log value | |
| A-1 | $1.13 \times 10^6$ | 6.05 | $1.10 \times 10^2$ | 2.04 | 0.0 |
| B-1 | $1.80 \times 10^5$ | 5.26 | $4.40 \times 10^3$ | 3.64 | 2.4 |
| C-1 | $1.05 \times 10^6$ | 6.02 | $4.39 \times 10^4$ | 4.64 | 4.0 |
| D-1 | $1.02 \times 10^6$ | 6.01 | $3.28 \times 10^5$ | 5.52 | 24.3 |
| E-1 | $7.89 \times 10^5$ | 5.9 | $6.11 \times 10^5$ | 5.79 | 43.6 |
| F-1 | $3.63 \times 10^5$ | 5.56 | $9.08 \times 10^5$ | 5.96 | 71.5 |
| G-1 | $3.39 \times 10^4$ | 4.53 | $1.25 \times 10^6$ | 6.1 | 97.4 |
| H-1 | 0 | 0 | $9.15 \times 10^5$ | 5.96 | 100.0 |

<Direct Sequencing>

Each of the samples A-1 to H-1 was subjected to direct sequencing with Sanger's deoxy method using 3730XL DNA ANALYZER (product of Applied Biosystems) as a sequencer and BIGDYE TERMINATOR v 3.1. (product of Applied Biosystems) as a reagent. Results are presented in FIG. 1.

In FIG. 1, a position indicated by the arrow denotes a base at position 277 in the base sequence coding for the NS5A protein. Base sequences of the samples A-1 to H-1 were confirmed from results in FIG. 1.

From the results of the direct sequencing, it was confirmed that results of the real-time PCR were correct. As a result, it was indicated that the presence or absence of the mutation in the amino acid at position 93 of the HCV NS5A protein in a sample can be quantitatively measured at a low cost, easily, conveniently, and rapidly through the real-time PCR with the cycling probe method using the probes designed in Production Example 1 and the primer designed in Production Example 2.

Test Example 2

<Real-Time PCR>

The real-time PCR was performed using the probes designed in Production Example 1 and the primer designed in Production Example 2 in the same manner as in Test Example 1, except that Artificial synthetic gene-3 (mutated form: Y93H) prepared in Preparative Example 1 was used as a gene. Results are presented in Table 5.

TABLE 5

| Sample name | Measurement result Amino acid at position 93 | | | | Rate of mutation to Y93H in sample (%) |
|---|---|---|---|---|---|
| | Y | | H | | |
| | Copy number | Log value | Copy number | Log value | |
| Artificial synthetic gene-3 (Hcgc) | 0 | 0 | $2.41 \times 10^7$ | 7.38 | 100 |

From the results in Table 5, it was indicated that, when the probes designed in Production Example 1 were used, the Hcac type sequence (aa(c)gc(a)ca(c); sequence in which the bases described in parentheses in the base sequence set forth. SEQ ID NO: 13 are cac from the 5'-side) and, unexpectedly, the Hcgc type sequence ((aa(c)gc(g)ca(c); sequence in which the bases described in parentheses in the base sequence set forth in SEQ ID NO: 13 are cgc from the 5'-side) could be detected.

Therefore, it was indicated that, when the probe set designed in Production Example 1 was used, the presence or absence of the mutation in the amino acid at position 93 of various HCV NS5A proteins in a sample could be quantitatively measured at a low cost, easily, conveniently, and rapidly while suppressing an influence of mutations or variations in HCV.

Test Example 3

<Sample>

Fourteen samples were prepared from sera from patients infected with HCV (genotype: type 1b) (obtained from Society of SPI).

<Preparation of Viral RNA>

QIAAMP MINELUTE VIRUS SPIN KIT (product of QIAGEN N.V.) was used to extract and purify viral RNA from each of the samples.

<cDNA Synthesizing Step> cDNA SYNTHESIS KIT (M-MLV Version) (product of Takara Bio Inc.) was used to synthesize double-stranded cDNA using, as a template, the viral RNA.

<Real-Time PCR Step>

The real-time PCR was performed using the probes designed in Production Example 1 and the primer set designed in Production Example 2 in the same manner as in Test Example 1, except that the double-stranded cDNA synthesized in the cDNA synthesizing step was used as a template. Results are presented in Table 6.

<Direct Sequencing>

Direct sequencing was performed in the same manner as in Test Example 1, except that the double-stranded cDNA synthesized in the cDNA synthesizing step was used. Results are presented in Table 6.

TABLE 6

| Sample | Real-time PCR | | | | | Direct sequencing Measurement result Amino acid at position 93 |
|---|---|---|---|---|---|---|
| | Measurement result Amino acid at position 93 | | | | Rate of mutation to Y93H in sample (%) | |
| | Y | | H | | | |
| | Copy number | Log value | Copy number | Log value | | |
| 1 | 3,573 | 3.55 | 0 | 0.00 | 0 | Y |
| 2 | 161,411 | 5.21 | 0 | 0.00 | 0 | Y |
| 3 | 537,950 | 5.73 | 0 | 0.00 | 0 | Y |
| 4 | 0 | 0.00 | 707,261 | 5.85 | 100 | H |
| 5 | 183,033 | 5.26 | 0 | 0.00 | 0 | Y |
| 6 | 7,845 | 3.89 | 0 | 0.00 | 0 | Y |
| 7 | 185,173 | 5.27 | 0 | 0.00 | 0 | Y |
| 8 | 100,275 | 5.00 | 0 | 0.00 | 0 | Y |
| 9 | 51,548 | 4.71 | 0 | 0.00 | 0 | Y |
| 10 | 247 | 2.39 | 0 | 0.00 | 0 | Y |
| 11 | 218 | 2.34 | 0 | 0.00 | 0 | Y |
| 12 | 0 | 0.00 | 151,001 | 5.18 | 100 | H |
| 13 | 123,741 | 5.09 | 0 | 0.00 | 0 | Y |
| 14 | 10,576 | 4.02 | 0 | 0.00 | 0 | Y |

From the results of Table 6, it was confirmed that results of the real-time PCR were consistent with the results of the direct sequencing, that is, the results of the real-time PCR were correct.

The direct sequencing can qualitatively determine the presence or absence of the mutation, but cannot quantitatively determine the degree of mutation. In addition, it took about 12 hours from preparation of the viral RNA from the sample to obtain sequence results. On the other hand, the real-time PCR with the cycling probe method according to the present invention can quantitatively determine an amount of the mutation in addition to the presence or absence of the mutation. It took about 5 hours from preparation of the viral RNA from the sample to obtain results. That is, the results were obtained very rapidly.

Information on bases described in parentheses in the base sequence set forth in SEQ ID NO: 13 for Samples 1 to 14 are presented in the following Table 7.

TABLE 7

| Sample | Information on bases described in parentheses in base sequence set forth in SEQ ID NO: 13 (described from the 5'-side) | Amino acid at position 93 |
|---|---|---|
| 1 | cac | Y |
| 2 | cac | Y |
| 3 | cac | Y |
| 4 | cac | H |
| 5 | cac | Y |
| 6 | cgc | Y |
| 7 | cac | Y |
| 8 | cac | Y |
| 9 | cac | Y |
| 10 | ccc | Y |
| 11 | cgc | Y |
| 12 | cgc | H |
| 13 | cac | Y |
| 14 | cgc | Y |

From the results of Samples 6, 11, and 14, and 10 in Table 7, it was indicated that, when the probes designed in Production Example 1 were used, the Ycac type sequence; sequence in which the bases described in parentheses in the base sequence set forth in SEQ ID NO: 13 are cac from the 5'-side) and, unexpectedly, the Ycgc type sequence (sequence in which the bases described in parentheses in the base sequence set forth in SEQ ID NO: 13 are cgc from the 5'-side) and the Yccc type sequence (sequence in which the bases described in parentheses in the base sequence set forth in SEQ ID NO: 13 are ccc from the 5'-side) could be detected.

Similar to the results in Test Example 2, it was indicated from the result of Sample 12 that, when the probes designed in Production Example 1 were used, the Hcac type sequence (sequence in which the bases described in parentheses in the base sequence set forth in SEQ ID NO: 13 are cac from the 5'-side) and, unexpectedly, the Hcgc type sequence (sequence in which the bases described in parentheses in the base sequence set forth in SEQ ID NO: 13 are cgc from the 5'-side) could be detected.

Therefore, it was indicated that, when the probe set designed in Production Example 1 was used, the presence or absence of the mutation in the amino acid at position 93 of various HCV NS5A proteins in a sample could be quantitatively measured at a low cost, easily, conveniently, and rapidly while suppressing an influence of mutations or variations in HCV.

Test Example 4

<Sample>

One sample was prepared from serum from each of a patient infected with HCV (genotype: type 1a), a patient infected with HCV (genotype: type 2a), and a patient infected with HCV (genotype: type 2b) (all obtained from Society of SPI).

<Preparation of Viral RNA>

QIAAMP MINELUTE VIRUS SPIN KIT (product of QIAGEN N.V.) was used to extract and purify viral RNA from each of the samples.

<cDNA Synthesizing Step> cDNA SYNTHESIS KIT (M-MLV Version) (product of Takara Bio Inc.) was used to synthesize double-stranded cDNA using, as a template, the viral RNA.

<Real-Time PCR Step>

The real-time PCR was performed using the probes designed in Production Example 1 and the primer set designed in Production Example 2 in the same manner as in Test Example 1, except that the double-stranded cDNA synthesized in the cDNA synthesizing step was used as a template. Results are presented in Table 8.

<Direct Sequencing>

Direct sequencing was performed in the same manner as in Test Example 1, except that the double-stranded cDNA synthesized in the cDNA synthesizing step was used. Results are presented in Table 8.

TABLE 8

| | Real-time PCR | | | | | Direct sequencing Measurement result |
|---|---|---|---|---|---|---|
| | Measurement result Amino acid at position 93 | | | | Rate of mutation | |
| | Y | | H | | to Y93H | |
| Sample | Copy number | Log value | Copy number | Log value | in sample (%) | Amino acid at position 93 |
| Type 1a | 10,392 | 4.02 | 0 | 0.00 | 0 | Y |
| Type 2a | 7807 | 3.89 | 0 | 0.00 | 0 | Y |
| Type 2b | 349 | 2.54 | 0 | 0.00 | 0 | Y |

From the results of Table 8, it was confirmed that results of the real-time PCR were consistent with the results of the direct sequencing, that is, the results of the real-time PCR were correct.

Comparative Production Example 1: Probe

The following probe was designed in the same manner as SEQ ID NO: 2, except that the base at position 277 contributing to the mutation in the amino acid at position 93 of the NS5A protein was determined as the RNA moiety of the probe.

—Probe—

Hcac Type-2:

(SEQ ID NO: 17)
5'-aacgca[c]aca-3'

In SEQ ID NO: 17, the base c described in brackets denotes RNA, and the underlined part denotes a sequence corresponding to the region coding for the amino acid at position 93 of the NS5A protein. The Hcac type-2 has a sequence in which the amino acid at position 93 of the NS5A was histidine and the bases described in parentheses in the base sequence set forth in SEQ ID NO: 13 were cac from the 5'-side.

The Hcac type-2 probe was modified with a fluorescent substance (FAM) at the 5'-terminus and with a quenching substance (ECLIPSE DARK QUENCHER (product of Epoch Biosciences)) at the 3'-terminus.

Test Example 5

The real-time PCR was performed in the same manner as in Test Example 1, except that the following combinations were used. Note that, each Artificial synthetic gene was used for the real-time PCR in an amount (number of molecules) of $2.00 \times 10^6$. Results are presented in Table 9.

Test Example 5-1

Artificial synthetic gene: Artificial synthetic gene-3 (SEQ ID NO: 16, mutated form, a sequence in which the bases described in parentheses in the base sequence set forth in SEQ ID NO: 13 were cgc from the 5'-side).
Probe: Hcac type-2 (SEQ ID NO: 17, RNA at position 277, mutated form, a sequence in which the bases described in parentheses in the base sequence set forth in SEQ ID NO: 13 were cac from the 5'-side).
Primer: Primer set in Production Example 2.

Test Example 5-2

Artificial synthetic gene: Artificial synthetic gene-3 (SEQ ID NO: 16, mutated form, a sequence in which the bases described in parentheses in the base sequence set forth in SEQ ID NO: 13 were cgc from the 5'-side).
Probe: Hcac type-1 (SEQ ID NO: 2, RNA at position 278, mutated form, a sequence in which the bases described in parentheses in the base sequence set forth in SEQ ID NO: 13 were cac from the 5'-side).
Primer: Primer set in Production Example 2.

Test Example 5-3

Artificial synthetic gene: Artificial synthetic gene-2 (SEQ ID NO: 15, mutated form, a sequence in which the bases described in parentheses in the base sequence set forth in SEQ ID NO: 13 were cac from the 5'-side).
Probe: Hcac type-2 (SEQ ID NO: 17, RNA at position 277, mutated form, a sequence in which the bases described in parentheses in the base sequence set forth in SEQ ID NO: 13 were cac from the 5'-side).
Primer: Primer set in Production Example 2.

Test Example 5-4

Artificial synthetic gene: Artificial synthetic gene-2 (SEQ ID NO: 15, mutated form, a sequence in which the bases described in parentheses in the base sequence set forth in SEQ ID NO: 13 were cac from the 5'-side).
Probe: Hcac type-1 (SEQ ID NO: 2, RNA at position 278, mutated form, a sequence in which the bases described in parentheses in the base sequence set forth in SEQ ID NO: 13 were cac from the 5'-side).
Primer: Primer set in Production Example 2.

TABLE 9

| Test Example | Artificial synthetic gene | Probe (Position of RNA) | Real-time PCR Copy number | Log value |
|---|---|---|---|---|
| 5-1 | 3 (Hcgc) | Hcac-2 (at position 277) | 387 | 2.59 |
| 5-2 | 3 (Hcgc) | Hcac-1 (at position 278) | 300,000 | 5.48 |
| 5-3 | 2 (Hcac) | Hcac-2 (at position 277) | 2,410,000 | 6.38 |
| 5-4 | 2 (Hcac) | Hcac-1 (at position 278) | 2,920,000 | 6.47 |

It was be confirmed from Table 9 that although the probe of Comparative Production Example 1 (Hcac type-2) designed according to the typical cycling probe method was affected by variation of the base at position 276 coding for the NS5A protein, the probe according to the present invention (Hcac type-1) designed in Production Example 1 was, unexpectedly, able to detect the presence or absence of the mutation without being affected by variation of the base at position 276 coding for the NS5A protein.

Therefore, it was indicated that, when the real-time PCR was performed with the cycling probe method using the probe set designed in Production Example 1 and the primer set designed in Production Example 2, in various genotypes of HCV, the presence or absence of the mutation in the amino acid at position 93 of various HCV NS5A proteins in a sample could be quantitatively measured at a low cost, easily, conveniently, and rapidly while suppressing an influence of mutations or variations in HCVs with various genotypes.

Production Example 3: Probe

The following probe set was designed for the purpose of more improving the detection rate of the mutation in the amino acid at position 93 of the hepatitis C virus NS5A protein.

—Probe Set—

Probes for Detecting Wild-Type Strain:

(1)
(SEQ ID NO: 1)
5'-aacgcat[a]ca-3'

(2)
(SEQ ID NO: 9)
5'-aacgcgt[a]ca-3'

In SEQ ID NOs: 1 and 9, the base a described in brackets denotes RNA, and the underlined part denotes a sequence corresponding to the region coding for the amino acid at position 93 of the NS5A protein.

The probes for detecting wild-type strain having sequences set forth in SEQ ID NOs: 1 and 9 were modified with a fluorescent substance (FAM) at the 5'-terminus and with a quenching substance (ECLIPSE DARK QUENCHER (product of Epoch Biosciences)) at the 3'-terminus.

A ratio of the number of molecules of the probe as set forth in SEQ ID NO: 1 to the number of molecules of the probe as set forth in SEQ ID NO: 9 in the probes for detecting wild-type strain was 1:1.

Probes for Detecting Mutant Strain:

(SEQ ID NO: 18)
5'-acgcac[a]ca-3'

(SEQ ID NO: 22)
5'-acgcgc[a]ca-3'

In SEQ ID NOs: 18 and 22, the base a described in brackets denotes RNA, and the underlined part denotes a sequence corresponding to a region coding for the amino acid at position 93 of the NS5A protein.

The probes for detecting mutant strain having sequences set forth in SEQ ID NOs: 18 and 22 were modified with a fluorescent substance (ROX) at the 5'-terminus and with a quenching substance (ECLIPSE DARK QUENCHER (product of Epoch Biosciences)) at the 3'-terminus.

A ratio of the number of molecules of the probe as set forth in SEQ ID NO: 18 to the number of molecules of the probe as set firth in SEQ ID NO: 22 in the probe for detecting mutant strain was 1:1.

Test Example 6

<Preparation of Artificial Synthetic Gene Sample>

Artificial synthetic gene-4 (wild-type: Y93) and Artificial synthetic gene-3 (mutated form: Y93H) prepared in Preparative Example 1 were mixed together as described in Table 10 to thereby prepare samples of Artificial synthetic gene.

TABLE 10

| Sample name | Amount of Artificial synthetic gene (number of molecules) | | Mixed ratio of Artificial synthetic gene-3 (%) |
| --- | --- | --- | --- |
| | Artificial synthetic gene-4 (Ycgc) | Artificial synthetic gene-3 (Hcgc) | |
| A-2 | $1.00 \times 10^6$ | 0 | 0 |
| B-2 | $9.50 \times 10^5$ | $5.00 \times 10^4$ | 5 |
| C-2 | $9.00 \times 10^5$ | $1.00 \times 10^5$ | 10 |
| D-2 | $7.00 \times 10^5$ | $3.00 \times 10^5$ | 30 |
| E-2 | $5.00 \times 10^5$ | $5.00 \times 10^5$ | 50 |
| F-2 | $3.00 \times 10^5$ | $7.00 \times 10^5$ | 70 |
| G-2 | $1.00 \times 10^5$ | $9.00 \times 10^5$ | 90 |
| H-2 | 0 | $1.00 \times 10^6$ | 100 |

<Real-Time PCR>

For each of samples A-2 to H-2, the real-time PCR (reaction device: Light Cycler 480) was performed in a reaction liquid having the composition described below (see, Table 11) using the probes designed in Production Example 3, the primer set designed in Production Example 2, and CYCLEAVE (registered trademark) PCR REACTION MIX (product of Takara Bio Inc.) under the reaction conditions described below.

Note that, in the real-time PCR, the probes for detecting wild-type strain (Cycling probe Y) and the probes for detecting mutant strain (Cycling probe H) were placed into a single well, where the reaction was performed.

—Reaction Condition—
——Hold (Initial Denaturation)——
Number of cycle: 1
Condition: at 95° C. for 30 sec
——3-Step PCR——
Number of cycle: 45
Condition: at 95° C. for 5 sec, at 55° C. for 10 sec, and then at 72° C. for 25 sec.

TABLE 11

| <Per 1 reaction> | | |
| --- | --- | --- |
| Reagent | Used amount | Final concentration |
| CycleavePCR Reaction Mix (2 × conc.) | 12.5 μl | 1× |
| PCR Forward Primer (10 μM) | 2.5 μl | 1.0 μM |
| PCR Reverse Primer (10 μM) | 2.5 μl | 1.0 μM |
| Cycling probe Y (5 μM) | 1.0 μl | 0.2 μM |
| Cycling probe H (5 μM) | 1.0 μl | 0.2 μM |
| dH₂O (sterile distilled water) | 3.5 μl | |
| template | 2.0 μl | |
| total | 25.0 μl | |

From the results of the real-time PCR, the mutation in the amino acid at position 93 of the NS5A protein was quantified and a rate of mutation was calculated. Results are presented in Table 12.

TABLE 12

| | Measurement result Amino acid at position 93 | | | | Rate of |
| --- | --- | --- | --- | --- | --- |
| | Y | | H | | mutation to |
| Sample name | Copy number | Log value | Copy number | Log value | Y93H in sample (%) |
| A-2 | $4.09 \times 10^5$ | 5.61 | 0 | 0 | 0.0 |
| B-2 | $1.24 \times 10^6$ | 6.09 | $5.32 \times 10^4$ | 4.73 | 4.1 |
| C-2 | $1.16 \times 10^6$ | 6.06 | $1.51 \times 10^5$ | 5.18 | 11.5 |
| D-2 | $3.92 \times 10^5$ | 5.59 | $1.65 \times 10^5$ | 5.22 | 29.6 |
| E-2 | $1.00 \times 10^6$ | 6.00 | $8.38 \times 10^5$ | 5.92 | 45.6 |
| F-2 | $3.23 \times 10^5$ | 5.51 | $8.85 \times 10^5$ | 5.95 | 73.3 |
| G-2 | $1.88 \times 10^5$ | 5.27 | $1.59 \times 10^6$ | 6.20 | 89.4 |
| H-2 | 0 | 0 | $7.49 \times 10^5$ | 5.87 | 100.0 |

From the results of the real-time PCR, it was indicated that the presence or absence of the mutation in the amino acid at position 93 of the HCV NS5A protein in a sample could be detected at a higher accuracy when the probe set designed in Production Example 3 was used than when the probe set designed in Production Example 1 was used.

Test Example 7

The real-time PCR was performed using the probes designed in Production Example 3 and the primer designed in Production Example 2 in the same manner as in Test Example 6, except that Artificial synthetic gene-2 (mutated form: Y93H) prepared in Preparative Example 1 was used as a gene. Results are presented in Table 13.

TABLE 13

| | Measurement result Amino acid at position 93 | | | | Rate of |
| --- | --- | --- | --- | --- | --- |
| | Y | | H | | mutation to |
| Sample name | Copy number | Log value | Copy number | Log value | Y93H in sample (%) |
| Artificial synthetic gene-2 (Hcac) | 0 | 0 | $1.10 \times 10^6$ | 6.04 | 100 |

From the results of Table 13, it was indicated that, when the probe set designed in Production Example 3 was used, the Hcac type sequence (aa(c)gc(a)ca(c); sequence in which bases described in parentheses in the base sequence set forth in SEQ ID NO: 13 were cac from the 5'-side) could also be detected at a high accuracy in addition to the Hcgc type sequence (aa(c)gc(g)ca(c); sequence in which bases described in parentheses in the base sequence set forth in SEQ ID NO: 13 were cgc from the 5'-side).

Therefore, it was indicated that, when the probe set designed in Production Example 3 was used, the presence or absence of the mutation in the amino acid at position 93 of various HCV NS5A proteins in a sample could be measured at a higher accuracy while suppressing an influence of mutations or variations in HCV.

Aspects of the present invention are, for example, as follows:

<1> A method for detecting a mutation in an amino acid at position 93 of a hepatitis C virus NS5A protein, the method including:
synthesizing cDNA using, as a template, hepatitis C virus RNA in a sample; and
performing a real-time PCR with a cycling probe method using, as a template, the cDNA;
wherein a primer set used in the real-time PCR is a primer set which is designed to be able to amplify a region including a base sequence coding for the amino acid at position 93 of the hepatitis C virus NS5A protein, and
wherein probes used in the real-time PCR include:
a probe consisting of a base sequence set forth in the following SEQ ID NO: 1 or a probe consisting f a complementary base sequence thereof; and
at least one of a probe consisting of a base sequence set forth in the following SEQ ID NO: 2 or a probe consisting of a complementary base sequence thereof, and a probe consisting of a base sequence set forth in the following SEQ ID NO: 18 or a probe consisting of a complementary base sequence thereof:

aacgcat[a]ca (SEQ ID NO: 1)

aacgcac[a]ca (SEQ ID NO: 2)

acgcac[a]ca (SEQ ID NO: 18)

where in each of the SEQ ID NOs: 1, 2, and 18, a base described in brackets denotes RNA.

<2> The method for detecting a mutation an amino acid at position 93 of a hepatitis C virus NS5A protein according to <1>, wherein the probes used in the real-time PCR include:
a probe consisting of a base sequence set forth in the following SEQ ID NO: 9 or a probe consisting of a complementary base sequence thereof; and
at least one of a probe consisting of a base sequence set forth in the following SEQ ID NO: 10 or a probe consisting of a complementary base sequence thereof, and a probe consisting of a base sequence set forth in the following SEQ ID NO: 22 or a probe consisting of a complementary base sequence thereof:

aacgcgt[a]ca (SEQ ID NO: 9)

aacgcgc[a]ca (SEQ ID NO: 10)

acgcgc[a]ca (SEQ ID NO: 22)

where in each of the SEQ ID NOs: 9, 10, and 22, a base described in brackets denotes RNA.

<3> The method for detecting a mutation in an amino acid at position 93 of a hepatitis C virus NS5A protein according to <1> or <2>, wherein the probes used in the real-time PCR include:
a probe consisting of a base sequence set forth in the following SEQ ID NO: 3 or a probe consisting of a complementary base sequence thereof; and
at least one of a probe consisting of a base sequence set forth in the following SEQ ID NO: 4 or a probe consisting of a complementary base sequence thereof, and a probe consisting of a base sequence set forth in the following SEQ ID NO: 19 or a probe consisting of a complementary base sequence thereof:

aacgcat[a]ta (SEQ ID NO: 3)

aacgcac[a]ta (SEQ ID NO: 4)

acgcac[a]ta (SEQ ID NO: 19)

where in each of the SEQ ID NOs: 3, 4, and 19, a base described brackets denotes RNA.

<4> The method for detecting a mutation in an amino acid at position 93 of a hepatitis C virus NS5A protein according to any one of <1> to <3>, wherein the probes used in the real-time PCR include at least one of the following (1) and (2):

(1) a combination consisting of: a probe consisting of a base sequence set forth in the following SEQ ID NO: 5 or a probe consisting of a complementary base sequence thereof; and at least one of a probe consisting of a base sequence set forth in the following SEQ ID NO: 6 or a probe consisting of a complementary base sequence thereof, and a probe consisting of a base sequence set forth in the following SEQ ID NO: 20 or a probe consisting of a complementary base sequence thereof;

(2) a combination consisting of: a probe consisting of a base sequence set forth in the following SEQ ID NO: 7 or a probe consisting of a complementary base sequence thereof; and at least one of a probe consisting of a base sequence set forth in the following SEQ ID NO: 8 or a probe consisting of a complementary base sequence thereof, and a probe consisting of a base sequence set forth in the following SEQ ID NO: 21 or a probe consisting of a complementary base sequence thereof:

aatgcat[a]ca (SEQ ID NO: 5)

aatgcac[a]ca (SEQ ID NO: 6)

atgcac[a]ca (SEQ ID NO: 20)

aatgcat[a]ta (SEQ ID NO: 7)

aatgcac[a]ta (SEQ ID NO: 8)

atgcac[a]ta (SEQ ID NO: 21)

where in each of the SEQ ID NOs: 5, 6, 20, 7, 8, and 21, a base described in brackets denotes RNA.

<5> The method for detecting a mutation in an amino acid at position 93 of a hepatitis C virus NS5A protein according to any one of <1> to <4>, wherein the primer set used in the real-time PCR includes the following (1) or (2):
(1) a primer set consisting of a primer consisting of a base sequence set forth in the following SEQ ID NO: 11 and a primer consisting of a base sequence set forth in the following SEQ ID NO: 12;
(2) a primer set consisting of a primer consisting of a base sequence complementary to a base sequence set forth in the following SEQ ID NO: 11 and a primer consisting of a base sequence complementary to a base sequence set forth in the following SEQ ID NO: 12:

```
                                        (SEQ ID NO: 11)
    ggttccatgaggatcgttg (SEQ ID NO: 12)
    ccgtcacgtagtggaaatc.
```

<6> The method for detecting a mutation in an amino acid at position 93 of a hepatitis C virus NS5A protein according to any one of <1> to <5>, wherein the hepatitis C virus has a genotype of type 1a, type 1b, type 2a, or type 2b.

<7> A kit for detecting a mutation in an amino acid at position 93 of a hepatitis C virus NS5A protein, the kit including:
a probe consisting of a base sequence set forth in the following SEQ ID NO: 1 or a probe consisting of a complementary base sequence thereof; and
at least one of a probe consisting of a base sequence set forth in the following SEQ ID NO: 2 or a probe consisting of a complementary base sequence thereof, and a probe consisting of a base sequence set forth. In the following SEQ ID NO: 18 or a probe consisting of a complementary base sequence thereof:

```
                                        (SEQ ID NO: 1)
    aacgcat[a]ca (SEQ ID NO: 2)
    aacgcac[a]ca (SEQ ID NO: 18)
    acgcac[a]ca
``` where in each of the SEQ ID NOs: 1, 2, and 18, a base described in brackets denotes RNA.

<8> The kit for detecting a mutation in an amino acid at position 93 of a hepatitis C virus NS5A protein according to <7>, wherein the kit includes:
a probe consisting of a base sequence set forth in the following SEQ ID NO: 9 or a probe consisting of a complementary base sequence thereof; and
at least one of a probe consisting of a base sequence set forth in the following SEQ ID NO: 10 or a probe consisting of a complementary base sequence thereof, and a probe consisting of a base sequence set forth in the following SEQ ID NO: 22 or a probe consisting of a complementary base sequence thereof:

```
                                        (SEQ ID NO: 9)
    aacgcgt[a]ca (SEQ ID NO: 10)
    aacgcgc[a]ca (SEQ ID NO: 22)
    acgcgc[a]ca
``` where in each of the SEQ ID NOs: 9, 10, and 22, a base described in brackets denotes RNA.

<9> The kit for detecting a mutation in an amino acid at position 93 of a hepatitis C virus NS5A protein according to <7> or <8>, wherein the kit includes:
a probe consisting of a base sequence set forth in the following SEQ ID NO: 3 or a probe consisting of a complementary base sequence thereof; and
at least one of a probe consisting of a base sequence set forth in the following SEQ ID NO: 4 or a probe consisting of a complementary base sequence thereof, and a probe consisting of a base sequence set forth in the following SEQ ID NO: 19 or a probe consisting of a complementary base sequence thereof:

```
                                        (SEQ ID NO: 3)
    aacgcat[a]ta (SEQ ID NO: 4)
    aacgcac[a]ta (SEQ ID NO: 19)
    acgcac[a]ta
``` where in each of the SEQ ID NOs: 3, 4, and 19, a base described in brackets denotes RNA.

<10> The kit for detecting a mutation in an amino acid at position 93 of a hepatitis C virus NS5A protein according to any one of <7> to <9>, wherein the kit includes at least one of the following (1) and (2):
(1) a combination consisting of: a probe consisting of a base sequence set forth in the following SEQ ID NO: 5 or a probe consisting of a complementary base sequence thereof; and at least one of a probe consisting of a base sequence set forth in the following SEQ ID NO: 6 or a probe consisting of a complementary base sequence thereof, and a probe consisting of a base sequence set forth in the following SEQ ID NO: 20 or a probe consisting of a complementary base sequence thereof;
(2) a combination consisting of: a probe consisting of a base sequence set forth in the following SEQ ID NO: 7 or a probe consisting of a complementary base sequence thereof; and at least one of a probe consisting of a base sequence set forth in the SEQ ID NO: 8 or a probe consisting of a complementary base sequence thereof, and a probe consisting of a base sequence set forth in the following SEQ ID NO: 21 or a probe consisting of a complementary base sequence thereof:

```
                                        (SEQ ID NO: 5)
    aatgcat[a]ca (SEQ ID NO: 6)
    aatgcac[a]ca (SEQ ID NO: 20)
    atgcac[a]ca (SEQ ID NO: 7)
    aatgcat[a]ta (SEQ ID NO: 8)
    aatgcac[a]ta (SEQ ID NO: 21)
    atgcac[a]ta
``` where in each of the SEQ ID NOs: 5, 6, 20, 7, 8, and 21, a base described in brackets denotes RNA.

<11> The kit for detecting a mutation in an amino acid at position 93 of a hepatitis C virus NS5A protein according to any one of <7> to <10>, wherein the kit includes at least one of the following (1) and (2):

(1) a primer set consisting of a primer consisting of a base sequence set forth in the following SEQ ID NO: 11 and a primer consisting of a base sequence set forth in the following SEQ ID NO: 12;

(2) a primer set consisting of a primer consisting of a base sequence complementary to a base sequence set forth in the following SEQ ID NO: 11 and a primer consisting of a base sequence complementary to a base sequence set forth in the following SEQ ID NO: 12:

```
                                           (SEQ ID NO: 11)
             ggttccatgaggatcgttg (SEQ ID NO: 12)
             ccgtcacgtagtggaaatc.
```

<12> The kit for detecting a mutation in an amino acid at position 93 of a hepatitis C virus NS5A protein according to any one of <7> to <11>, wherein the hepatitis C virus has a genotype of type 1a, type 1b, type 2a, or type 2b.

INDUSTRIAL APPLICABILITY

A method for detecting a mutation in an amino acid at position 93 of a hepatitis C virus NS5A protein according to the present invention enables the presence or absence of a mutation in an amino acid at position 93 of various HCV NS5A proteins in a sample to be quantitatively measured at a low cost, easily, conveniently, and rapidly while suppressing an influence of mutations or variations in HCV. Therefore, the method can be suitably used for predicting efficacy of a drug which uses the mutation in the amino acid at position 93 of the NS5A protein as an index.

A kit for detecting a mutation in an amino acid at position 93 of a hepatitis C virus NS5A protein according to the present invention can be suitably used for the method for detecting a mutation in an amino acid at position 93 of a hepatitis C virus NS5A protein according to the present invention.

The invention claimed is:

1. A method for detecting a mutation in an amino acid at position 93 of a hepatitis C virus NS5A protein, the method comprising:
   synthesizing cDNA using, as a template, hepatitis C virus RNA in a sample; and
   performing a real-time PCR with a cycling probe method using, as a template, the cDNA;
   wherein a primer set used in the real-time PCR is a primer set which is designed to be able to amplify a region comprising the base sequence coding for the amino acid at position 93 of the hepatitis C virus NS5A protein, and wherein probes used in the real-time PCR comprise:
   a probe consisting of the base sequence of SEQ ID NO: 1 or the complement thereof; and
   at least one probe selected from
   a probe consisting of the base sequence of SEQ ID NO: 2 or the complement thereof, and
   a probe consisting of the base sequence of SEQ ID NO: 18 or the complement thereof:

aacgcat[a]ca (SEQ ID NO: 1)

aacgcac[a]ca (SEQ ID NO: 2)

acgcac[a]ca (SEQ ID NO: 18)

wherein each of the SEQ ID NOs: 1, 2, and 18, a base described in brackets denotes RNA.

2. The method for detecting a mutation in an amino acid at position 93 of a hepatitis C virus NS5A protein according to claim 1, wherein the probes used in the real-time PCR further comprise:
   a probe consisting of the base sequence of SEQ ID NO: 9 or the complement thereof;
   and at least one probe selected from a probe consisting of the base sequence of SEQ ID NO: 10 or the complement thereof, and a probe consisting of the base sequence of SEQ ID NO: 22 or the complement thereof:

aacgcgt[a]ca (SEQ ID NO: 9)

aacgcgc[a]ca (SEQ ID NO: 10)

acgcgc[a]ca (SEQ ID NO: 22)

wherein each of the SEQ ID NOs: 9, 10, and 22, a base described in brackets denotes RNA.

3. The method for detecting a mutation in an amino acid at position 93 of a hepatitis C virus NS5A protein according to claim 2, wherein the probes used in the real-time PCR further comprise:
   a probe consisting of the base sequence of SEQ ID NO: 3 or the complement thereof; and
   at least one probe selected from a probe consisting of the base sequence of SEQ ID NO: 4 or the complement thereof, and a probe consisting of the base sequence of SEQ ID NO: 19 or the complement thereof:

aacgcat[a]ta (SEQ ID NO: 3)

aacgcac[a]ta (SEQ ID NO: 4)

acgcac[a]ta (SEQ ID NO: 19)

wherein each of the SEQ ID NOs: 3, 4, and 19, a base described in brackets denotes RNA.

4. The method for detecting a mutation in an amino acid at position 93 of a hepatitis C virus NS5A protein according to claim 2, wherein the probes used in the real-time PCR further comprise at least one of the following (1) and (2):
   (1) a combination consisting of: a probe consisting of the base sequence of SEQ ID NO: 5 or the complement thereof; and
   at least one of a probe consisting of the base sequence of SEQ ID NO: 6 or the complement thereof, and
   a probe consisting of the base sequence of SEQ ID NO: 20 or the complement thereof;
   (2) a combination consisting of: a probe consisting of the base sequence of SEQ ID NO: 7 or the complement thereof; and
   at least one of a probe consisting of the base sequence of SEQ ID NO: 8 or the complement thereof, and a probe consisting of the base sequence of SEQ ID NO: 21 or the complement thereof:

aatgcat[a]ca (SEQ ID NO: 5)

aatgcac[a]ca (SEQ ID NO: 6)

atgcac[a]ca (SEQ ID NO: 20)

aatgcat[a]ta (SEQ ID NO: 7)

aatgcac[a]ta (SEQ ID NO: 8)

atgcac[a]ta (SEQ ID NO: 21)

wherein each of the SEQ ID NOs: 5, 6, 20, 7, 8, and 21, a base described in brackets denotes RNA.

5. The method for detecting a mutation in an amino acid at position 93 of a hepatitis C virus NS5A protein according to claim 2, wherein the primer set used in the real-time PCR is the following (1):
   (1) a primer set consisting of a primer consisting of the base sequence of SEQ ID NO: 11 and a primer consisting of the base sequence of SEQ ID NO: 12:

ggttccatgaggatcgttg (SEQ ID NO: 11)

ccgtcacgtagtggaaatc. (SEQ ID NO: 12)

6. The method for detecting a mutation in an amino acid at position 93 of a hepatitis C virus NS5A protein according to claim 1, wherein the probes used in the real-time PCR further comprise:
   a probe consisting of the base sequence of SEQ ID NO: 3 or the complement thereof; and
   at least one probe selected from a probe consisting of the base sequence of SEQ ID NO: 4 or the complement thereof, and a probe consisting of the base sequence of SEQ ID NO: 19 or the complement thereof:

```
                                         (SEQ ID NO: 3)
aacgcat[a]ta (SEQ ID NO: 4)
aacgcac[a]ta (SEQ ID NO: 19)
acgcac[a]ta
``` wherein each of the SEQ ID NOs: 3, 4, and 19, a base described in brackets denotes RNA.

7. The method for detecting a mutation in an amino acid at position 93 of a hepatitis C virus NS5A protein according to claim 6, wherein the probes used in the real-time PCR further comprise at least one of the following (1) and (2):
(1) a combination consisting of: a probe consisting of the base sequence of SEQ ID NO: 5 or the complement thereof; and
at least one probe selected from a probe consisting of the base sequence of SEQ ID NO: 6 or the complement thereof, and a probe consisting of the base sequence of SEQ ID NO: 20 or the complement thereof;
(2) a combination consisting of: a probe consisting of the base sequence of SEQ ID NO: 7 or the complement thereof; and
at least one probe selected from a probe consisting of the base sequence of SEQ ID NO: 8 or the complement thereof, and a probe consisting of the base sequence of SEQ ID NO: 21 or the complement thereof:

```
                                         (SEQ ID NO: 5)
aatgcat[a]ca (SEQ ID NO: 6)
aatgcac[a]ca (SEQ ID NO: 20)
atgcac[a]ca (SEQ ID NO: 7)
aatgcat[a]ta (SEQ ID NO: 8)
aatgcac[a]ta (SEQ ID NO: 21)
atgcac[a]ta
``` wherein each of the SEQ ID NOs: 5, 6, 20, 7, 8, and 21, a base described in brackets denotes RNA.

8. The method for detecting a mutation in an amino acid at position 93 of a hepatitis C virus NS5A protein according to claim 6, wherein the primer set used in the real-time PCR is the following (1):
(1) a primer set consisting of a primer consisting of the base sequence of SEQ ID NO: 11 and a primer consisting of the base sequence of SEQ ID NO: 12:

```
                                        (SEQ ID NO: 11)
ggttccatgaggatcgttg (SEQ ID NO: 12)
ccgtcacgtagtggaaatc.
```

9. The method for detecting a mutation in an amino acid at position 93 of a hepatitis C virus NS5A protein according to claim 1, wherein the probes used in the real-time PCR further comprise at least one of the following (1) and (2):

(1) a combination consisting of: a probe consisting of the base sequence of SEQ ID NO: 5 or the complement thereof; and
at least one probe selected from a probe consisting of the base sequence of SEQ ID NO: 6 or the complement thereof, and a probe consisting of the base sequence of SEQ ID NO: 20 or the complement thereof;
(2) a combination consisting of:
a probe consisting of the base sequence of SEQ ID NO: 7 or the complement thereof;
and at least one probe selected from a probe consisting of the base sequence of SEQ ID NO: 8 or the complement thereof, and a probe consisting of the base sequence of SEQ ID NO: 21 or the complement thereof:

```
                                         (SEQ ID NO: 5)
aatgcat[a]ca (SEQ ID NO: 6)
aatgcac[a]ca (SEQ ID NO: 20)
atgcac[a]ca (SEQ ID NO: 7)
aatgcat[a]ta (SEQ ID NO: 8)
aatgcac[a]ta (SEQ ID NO: 21)
atgcac[a]ta
``` wherein each of the SEQ ID NOs: 5, 6, 20, 7, 8, and 21, a base described in brackets denotes RNA.

10. The method for detecting a mutation in an amino acid at position 93 of a hepatitis C virus NS5A protein according to claim 1, wherein the primer set used in the real-time PCR is the following (1):
(1) a primer set consisting of a primer consisting of the base sequence of SEQ ID NO: 11 and a primer consisting of the base sequence of SEQ ID NO: 12:

```
                                        (SEQ ID NO: 11)
ggttccatgaggatcgttg (SEQ ID NO: 12)
ccgtcacgtagtggaaatc.
```

11. A kit for detecting a mutation in an amino acid at position 93 of a hepatitis C virus NS5A protein, the kit comprising:
a probe consisting of the base sequence of SEQ ID NO: 1 or the complement thereof;
and at least one probe selected from a probe consisting of the base sequence of SEQ ID NO: 2 or the complement thereof, and
a probe consisting of the base sequence of SEQ ID NO: 18 or the complement thereof:

```
                                         (SEQ ID NO: 1)
aacgcat[a]ca (SEQ ID NO: 2)
aacgcac[a]ca (SEQ ID NO: 18)
acgcac[a]ca
``` wherein each of the SEQ ID NOs: 1, 2, and 18, a base described in brackets denotes RNA and the other bases denote DNA.

12. The kit for detecting a mutation in an amino acid at position 93 of a hepatitis C virus NS5A protein according to claim 11, wherein the kit further comprises:

a probe consisting of the base sequence of SEQ ID NO: 9 or the complement thereof; and at least one probe selected from a probe consisting of the base sequence of SEQ ID NO: 10 or the complement thereof, and a probe consisting of the base sequence of SEQ ID NO: 22 or the complement thereof:

```
                              (SEQ ID NO: 9)
       aacgcgt[a]ca (SEQ ID NO: 10)
       aacgcgc[a]ca (SEQ ID NO: 22)
       acgcgc[a]ca
``` wherein each of the SEQ ID NOs: 9, 10, and 22, a base described in brackets denotes RNA and the other bases denote DNA.

13. The kit for detecting a mutation in an amino acid at position 93 of a hepatitis C virus NS5A protein according to claim 12, wherein the kit further comprises:

a probe consisting of the base sequence of SEQ ID NO: 3 or the complement thereof; and at least one probe selected from a probe consisting of the base sequence of SEQ ID NO: 4 or the complement thereof, and a probe consisting of the base sequence of SEQ ID NO: 19 or the complement thereof:

```
                              (SEQ ID NO: 3)
       aacgcat[a]ta (SEQ ID NO: 4)
       aacgcac[a]ta (SEQ ID NO: 19)
       acgcac[a]ta
``` wherein each of the SEQ ID NOs: 3, 4, and 19, a base described in brackets denotes RNA and the other bases denote DNA.

14. The kit for detecting a mutation in an amino acid at position 93 of a hepatitis C virus NS5A protein according to claim 12, wherein the kit further comprises at least one of the following (1) and (2):

(1) a combination consisting of: a probe consisting of the base sequence of SEQ ID NO: 5 or the complement thereof; and at least one probe selected from a probe consisting of the base sequence of SEQ ID NO: 6 or the complement thereof, and a probe consisting of the base sequence of SEQ ID NO: 20 or the complement thereof;

(2) a combination consisting of: a probe consisting of the base sequence of SEQ ID NO: 7 or the complement thereof; and at least one probe selected from a probe consisting of the base sequence of SEQ ID NO: 8 or the complement thereof, and a probe consisting of the base sequence of SEQ ID NO: 21 or the complement thereof:

```
                              (SEQ ID NO: 5)
       aatgcat[a]ca (SEQ ID NO: 6)
       aatgcac[a]ca (SEQ ID NO: 20)
       atgcac[a]ca (SEQ ID NO: 7)
       aatgcat[a]ta (SEQ ID NO: 8)
       aatgcac[a]ta (SEQ ID NO: 21)
       atgcac[a]ta
``` wherein each of the SEQ ID NOs: 5, 6, 20, 7, 8, and 21, a base described in brackets denotes RNA and the other bases denote DNA.

15. The kit for detecting a mutation in an amino acid at position 93 of a hepatitis C virus NS5A protein according to claim 12, wherein the kit further comprises the following (1):

(1) a primer set consisting of a primer consisting of the base sequence of SEQ ID NO: 11 and a primer consisting of the base sequence of SEQ ID NO: 12:

```
                              (SEQ ID NO: 11)
       ggttccatgaggatcgttg (SEQ ID NO: 12)
       ccgtcacgtagtggaaatc.
```

16. The kit for detecting a mutation in an amino acid at position 93 of a hepatitis C virus NS5A protein according to claim 11, wherein the kit further comprises:

a probe consisting of the base sequence of SEQ ID NO: 3 or the complement thereof; and at least one probe selected from a probe consisting of the base sequence of SEQ ID NO: 4 or the complement thereof, and a probe consisting of the base sequence of SEQ ID NO: 19 or the complement thereof:

```
                              (SEQ ID NO: 3)
       aacgcat[a]ta (SEQ ID NO: 4)
       aacgcac[a]ta (SEQ ID NO: 19)
       acgcac[a]ta
``` wherein each of the SEQ ID NOs: 3, 4, and 19, a base described in brackets denotes RNA and the other bases denote DNA.

17. The kit for detecting a mutation in an amino acid at position 93 of a hepatitis C virus NS5A protein according to claim 16, wherein the kit further comprises at least one of the following (1) and (2):

(1) a combination consisting of:

a probe consisting of the base sequence of SEQ ID NO: 5 or the complement thereof; and at least one probe selected from a probe consisting of the base sequence of SEQ ID NO: 6 or the complement thereof, and a probe consisting of the base sequence of SEQ ID NO: 20 or the complement thereof;

(2) a combination consisting of: a probe consisting of the base sequence of SEQ ID NO: 7 or the complement thereof; and at least one probe selected from a probe consisting of the base sequence of SEQ ID NO: 8 or the complement thereof, and a probe consisting of the base sequence of SEQ ID NO: 21 or the complement thereof:

```
aatgcat[a]ca                    (SEQ ID NO: 5)

aatgcac[a]ca                    (SEQ ID NO: 6)

atgcac[a]ca                     (SEQ ID NO: 20)

aatgcat[a]ta                    (SEQ ID NO: 7)

aatgcac[a]ta                    (SEQ ID NO: 8)

atgcac[a]ta                     (SEQ ID NO: 21)
``` wherein each of the SEQ ID NOs: 5, 6, 20, 7, 8, and 21, a base described in brackets denotes RNA and the other bases denote DNA.

18. The kit for detecting a mutation in an amino acid at position 93 of a hepatitis C virus NS5A protein according to claim 16, wherein the kit further comprises the following (1):
   (1) a primer set consisting of a primer consisting of the base sequence of SEQ ID NO: 11 and a primer consisting of the base sequence of SEQ ID NO: 12:

```
ggttccatgaggatcgttg             (SEQ ID NO: 11)

ccgtcacgtagtggaaatc.            (SEQ ID NO: 12)
```

19. The kit for detecting a mutation in an amino acid at position 93 of a hepatitis C virus NS5A protein according to claim 11, wherein the kit further comprises at least one of the following (1) and (2):
   (1) a combination consisting of: a probe consisting of the base sequence of SEQ ID NO: 5 or the complement thereof; and at least one probe selected from a probe consisting of the base sequence of SEQ ID NO: 6 or the complement thereof, and a probe consisting of the base sequence of SEQ ID NO: 20 or the complement thereof;
   (2) a combination consisting of:
   a probe consisting of the base sequence of SEQ ID NO: 7 or the complement thereof; and
   at least one probe selected from a probe consisting of the base sequence of SEQ ID NO: 8 or the complement thereof, and a probe consisting of the base sequence of SEQ ID NO: 21 or the complement thereof:

```
aatgcat[a]ca                    (SEQ ID NO: 5)

aatgcac[a]ca                    (SEQ ID NO: 6)

atgcac[a]ca                     (SEQ ID NO: 20)

aatgcat[a]ta                    (SEQ ID NO: 7)

aatgcac[a]ta                    (SEQ ID NO: 8)

atgcac[a]ta                     (SEQ ID NO: 21)
``` wherein each of the SEQ ID NOs: 5, 6, 20, 7, 8, and 21, a base described in brackets denotes RNA and the other bases denote DNA.

20. The kit for detecting a mutation in an amino acid at position 93 of a hepatitis C virus NS5A protein according to claim 11, wherein the kit further comprises the following (1):
   (1) a primer set consisting of a primer consisting of the base sequence of SEQ ID NO: 11 and a primer consisting of the base sequence of SEQ ID NO: 12:

```
ggttccatgaggatcgttg             (SEQ ID NO: 11)

ccgtcacgtagtggaaatc.            (SEQ ID NO: 12)
```

* * * * *

SEQUENCE LISTING

```
<160> NUMBER OF SEQ ID NOS: 23

<210> SEQ ID NO 1
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 1
aacgcataca                                                           10

<210> SEQ ID NO 2
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 2
aacgcacaca                                                           10

<210> SEQ ID NO 3
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 3
aacgcatata                                                           10
```

```
<210> SEQ ID NO 4
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 4
aacgcacata                                                                10

<210> SEQ ID NO 5
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 5
aatgcataca                                                                10

<210> SEQ ID NO 6
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 6
aatgcacaca                                                                10

<210> SEQ ID NO 7
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 7
aatgcatata                                                                10

<210> SEQ ID NO 8
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 8
aatgcacata                                                                10
```

<210> SEQ ID NO 9
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 9
aacgcgtaca                                                          10

<210> SEQ ID NO 10
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (8)..(8)
<223> OTHER INFORMATION: This "a" is RNA

<400> SEQUENCE: 10
aacgcgcaca                                                          10

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
ggttccatga ggatcgttg                                                19

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
ccgtcacgta gtggaaatc                                                19

<210> SEQ ID NO 13
<211> LENGTH: 9
<212> TYPE: DNA
<213> ORGANISM: hepatitis C virus
<220> FEATURE:
<221> NAME/KEY: misc_feature
<222> LOCATION: (6)..(6)
<223> OTHER INFORMATION: n stands for any base

<400> SEQUENCE: 13 aaygcnyay                                                           9

<210> SEQ ID NO 14
<211> LENGTH: 207
<212> TYPE: DNA
<213> ORGANISM: hepatitis C virus

<400> SEQUENCE: 14
tgtcaaaaac ggttccatga ggatcgttgg gcctaaaacc tgcagcaaca cgtggcatgg    60

```
aacattcccc atcaacgcat acaccacggg cccctgcaca ccctcccgg cgccaaacta      120 ttccagggcg ctgtggcggg tggctgctga ggagtacgtg gaggttacgc gggtggggga      180
tttccactac gtgacgggca tgaccac                                          207
```

<210> SEQ ID NO 15
<211> LENGTH: 207
<212> TYPE: DNA
<213> ORGANISM: hepatitis C virus

<400> SEQUENCE: 15

```
tgtcaaaaac ggttccatga ggatcgttgg gcctaaaacc tgcagcaaca cgtggcatgg      60
aacattcccc atcaacgcac acaccacggg cccctgcaca ccctcccgg cgccaaacta      120 ttccagggcg ctgtggcggg tggctgctga ggagtacgtg gaggttacgc gggtggggga      180
tttccactac gtgacgggca tgaccac                                          207
```

<210> SEQ ID NO 16
<211> LENGTH: 207
<212> TYPE: DNA
<213> ORGANISM: hepatitis C virus

<400> SEQUENCE: 16

```
tgtcaaaaac ggttccatga ggatcgttgg gcctaaaacc tgcagcaaca cgtggcatgg      60
aacattcccc atcaacgcgc acaccacggg cccctgcaca ccctcccgg cgccaaacta      120 ttccagggcg ctgtggcggg tggctgctga ggagtacgtg gaggttacgc gggtggggga      180
tttccactac gtgacgggca tgaccac                                          207
```

<210> SEQ ID NO 17
<211> LENGTH: 10
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: This "c" is RNA

<400> SEQUENCE: 17

```
aacgcacaca                                                             10
```

<210> SEQ ID NO 18
<211> LENGTH: 9
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: This "a" is RNA

<400> SEQUENCE: 18

```
acgcacaca                                                              9
```

<210> SEQ ID NO 19
<211> LENGTH: 9
<212> TYPE: DNA
<213> ORGANISM: Artificial Sequence
<220> FEATURE:
<223> OTHER INFORMATION: probe
<220> FEATURE:

```
<221> NAME/KEY: misc_feature
<222> LOCATION: (7)..(7)
<223> OTHER INFORMATION: This "a" is RNA

<400> SEQUENCE: 19 acgcacata                                                                 9

<210> SEQ ID NO 20
<211> LENGTH: 9
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: This "a" is RNA

<400> SEQUENCE: 20 atgcacaca                                                                 9

<210> SEQ ID NO 21
<211> LENGTH: 9
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: This "a" is RNA

<400> SEQUENCE: 21 atgcacata                                                                 9

<210> SEQ ID NO 22
<211> LENGTH: 9
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (7)..(7)
<223> OTHER INFORMATION: This "a" is RNA

<400> SEQUENCE: 22 acgcgcaca                                                                 9

<210> SEQ ID NO 23
<211> LENGTH: 207
<212> TYPE: DNA
<213> ORGANISM: hepatitis C virus

<400> SEQUENCE: 23
tgtcaaaaac ggttccatga ggatcgttgg gcctaaaacc tgcagcaaca cgtggcatgg        60
aacattcccc atcaacgcgt acaccacggg cccctgcaca ccctcccgg cgccaaacta       120 ttccagggcg ctgtggcggg tggctgctga ggagtacgtg gaggttacgc gggtggggga       180
tttccactac gtgacgggca tgaccac                                           207
```